United States Patent
Feitisch et al.

(10) Patent No.: US 8,953,165 B2
(45) Date of Patent: *Feb. 10, 2015

(54) VALIDATION AND CORRECTION OF SPECTROMETER PERFORMANCE USING A VALIDATION CELL

(75) Inventors: Alfred Feitisch, Los Gatos, CA (US); Lutz Keller, Fontana, CA (US); Xiang Liu, Rancho Cucamonga, CA (US); Mathias Schrempel, Alta Loma, CA (US); Keith Benjamin Helbley, Riverside, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 382 days.

This patent is subject to a terminal disclaimer.

(21) Appl. No.: 13/027,000

(22) Filed: Feb. 14, 2011

(65) Prior Publication Data

US 2011/0299084 A1 Dec. 8, 2011

Related U.S. Application Data

(60) Provisional application No. 61/405,589, filed on Oct. 21, 2010.

(51) Int. Cl.
  *G01N 21/27* (2006.01)
  *G01J 3/28* (2006.01)
  (Continued)

(52) U.S. Cl.
  CPC .... *G01J 3/28* (2013.01); *G01J 3/42* (2013.01); *G01N 21/031* (2013.01); *G01N 21/31* (2013.01);
  (Continued)

(58) Field of Classification Search
  CPC ... G01N 21/39; G01N 21/31; G01N 21/3504; G01N 21/1702; G01N 21/0303; G01N 33/497; G01N 2021/1704; G01J 3/28; G01J 3/42
  USPC ........ 356/432–440, 243.1–243.8, 326; 95/90, 95/136, 235; 250/573, 574, 576
  See application file for complete search history.

(56) References Cited

U.S. PATENT DOCUMENTS 3,732,017 A  5/1973 Wolber
4,037,448 A  7/1977 Di Maio et al.
(Continued)

FOREIGN PATENT DOCUMENTS

CN  1900696 A  1/2007
EP  1111369 A1  6/2001
(Continued)

OTHER PUBLICATIONS

International Search Report and Written Opinion dated Feb. 2, 2012, for corresponding PCT Application No. PCT/US2011/057370.
(Continued)

*Primary Examiner* — Hoa Pham
(74) *Attorney, Agent, or Firm* — Mintz Levin Cohn Ferris Glovsky and Popeo, P.C.

(57) ABSTRACT

Light intensity data quantifying intensity of light generated by a light source and received at a detector during a validation mode of an absorption spectrometer can be compared with a stored data set representing at least one previous measurement in a validation mode of an analytical system. The validation mode can include causing the light to pass at least once through each of a zero gas and a reference gas contained within a validation cell and including a known amount of a target analyte. The zero gas can have at least one of known and negligible first light absorbance characteristics within a range of wavelengths produced by the light source. A validation failure can be determined to have occurred if the first light intensity data and the stored data set are out of agreement by more than a predefined threshold amount. Related systems, methods, and articles of manufacture are also described.

27 Claims, 14 Drawing Sheets

(51) Int. Cl.
*G01J 3/42* (2006.01)
*G01N 21/03* (2006.01)
*G01N 21/31* (2006.01)
*G01N 21/3504* (2014.01)
*G01N 21/3518* (2014.01)
*G01N 21/39* (2006.01)

(52) U.S. Cl.
CPC ........ G01N 21/3504 (2013.01); G01N 21/3518 (2013.01); G01N 21/39 (2013.01); *G01N 21/274* (2013.01); *G01N 2021/399* (2013.01)
USPC .................................... 356/437; 356/243.1

(56) References Cited

U.S. PATENT DOCUMENTS

| | | | |
|---|---|---|---|
| 4,253,770 A * | 3/1981 | Horiba | 356/433 |
| 4,937,448 A * | 6/1990 | Mantz et al. | 250/343 |
| 5,026,991 A | 6/1991 | Goldstein et al. | |
| 5,070,246 A | 12/1991 | Durham et al. | |
| 5,387,971 A * | 2/1995 | Koashi et al. | 356/246 |
| 5,502,308 A | 3/1996 | Wong | |
| 5,747,809 A * | 5/1998 | Eckstrom | 250/345 |
| 5,764,354 A * | 6/1998 | Aidam et al. | 356/243.1 |
| 6,064,488 A | 5/2000 | Brand et al. | |
| 6,449,040 B1 | 9/2002 | Fujita | |
| 6,486,474 B1 * | 11/2002 | Owen et al. | 250/339.02 |
| 6,636,316 B1 * | 10/2003 | Matsumoto et al. | 356/437 |
| 6,710,347 B1 | 3/2004 | Eden | |
| 6,967,322 B2 * | 11/2005 | Jones et al. | 250/269.1 |
| 7,180,595 B2 | 2/2007 | Willing et al. | |
| 7,352,464 B2 | 4/2008 | Chen et al. | |
| 7,704,301 B2 | 4/2010 | Zhou et al. | |
| 7,847,944 B2 * | 12/2010 | Buettner et al. | 356/436 |
| 8,035,816 B2 | 10/2011 | Randow et al. | |
| 8,152,900 B2 * | 4/2012 | Zhou et al. | 95/90 |
| 8,358,417 B2 * | 1/2013 | Feitisch et al. | 356/440 |
| 2003/0134427 A1 | 7/2003 | Roller et al. | |
| 2003/0178589 A1 * | 9/2003 | Mori et al. | 250/573 |
| 2003/0189709 A1 | 10/2003 | Maynard et al. | |
| 2007/0081162 A1 * | 4/2007 | Roller et al. | 356/437 |
| 2007/0195318 A1 | 8/2007 | Yamamoto | |
| 2008/0255769 A1 * | 10/2008 | Zhou et al. | 702/24 |
| 2008/0304066 A1 | 12/2008 | Kluczynski et al. | |
| 2010/0002234 A1 * | 1/2010 | Cormier et al. | 356/436 |

FOREIGN PATENT DOCUMENTS

| | | |
|---|---|---|
| EP | 1850112 A1 | 10/2007 |
| EP | 1990629 A1 | 11/2008 |
| GB | 2237630 A * | 5/1991 |
| GB | 2264169 A | 8/1993 |
| JP | 2009216385 A | 9/2009 |

OTHER PUBLICATIONS

International Search Report and Written Opinion dated Nov. 29, 2011, for corresponding international application No. PCT/US2011/024919.

* cited by examiner

VALIDATION AND CORRECTION OF SPECTROMETER PERFORMANCE USING A VALIDATION CELL

CROSS-REFERENCE TO RELATED APPLICATIONS

The current application claims priority under 35 U.S.C. §119(e) to U.S. Provisional Application Ser. No. 61/405,589, filed on Oct. 21, 2010. This application is related to co-pending and co-owned U.S. patent application Ser. No. 13/026,921, filed on Feb. 14, 2011, and entitled "Spectrometer with Validation Cell." The disclosures of the priority application and related application are each incorporated by reference herein in their entireties.

TECHNICAL FIELD

The subject matter described herein relates to quantifying gas-phase concentrations of chemical analytes, for example using spectroscopic analysis systems that include a validation cell that contains one or more reference gases or a full or partial vacuum.

BACKGROUND

Trace gas analyzers can require periodic validation of long term fidelity of the concentration measurements they generate, for example with respect to the performance of an analyzer relative to factory calibration or relative to a standard which is traceable to a national or international bureau of standards (e.g. including but not limited to the National Institute of Standards and Technology). Currently available solutions for in-field measurement validation typically include the use of permeation tube devices or calibrations performed using reference samples provided from a compressed gas cylinder.

Frequency stabilization of a tunable laser light source can be critical for quantitative trace gas absorption spectroscopy. Depending on the operational wavelength, a tunable laser source such as a diode laser can typically exhibit a wavelength drift on the order of a few picometers (on the order of gigahertz) per day to fractions of picometers per day. A typical trace gas absorption band linewidth can in some instances be on the order of a fraction of a nanometer to microns. Thus, drift of the laser light source can, over time, introduce critical errors in identification and quantification of trace gas analytes, particularly in gas having one or more background compounds whose absorption spectra might interfere with absorption features of a target analyte.

Permeation tube based validation systems are generally costly and complex and typically require very precise control of temperature and gas flow rates and elimination of temperature gradients across the permeation tube to provide an accurate result. Aging and contamination of permeation tube devices can alter the permeation rate over time, thereby causing a change in the validation measurement reading and potentially rendering the validation inaccurate over time. This problem can be addressed, albeit at potentially substantial expense, by frequent replacement of the permeation tube device. Further challenges can arise in the replacement of permeation tube devices in the field, as it can be difficult to correlate the trace gas concentration generated by a replacement permeation device to a bureau of standards traceable analyzer calibration. Permeation-based validation systems can also require a significant amount of carrier gas and analyte gas to prepare the validation gas stream. Permeation-based devices generally are not feasible when very reactive or corrosive gases are involved. Furthermore, permeation-based devices generally cannot accurately prepare low concentration (e.g., less than 10 parts per million and particularly on the order of parts per billion or smaller) validation streams for trace analyte measurements. A validation stream should advantageously remain accurate over a practical operating temperature range. Extreme temperature sensitivity of permeation devices can be a key challenge. For example, temperature changes of as little as 0.1° C. can cause moisture concentration changes of magnitude greater than ±10% of the nominal validation concentration, which is generally not acceptable for in field analyzer validation.

Validation using a reference gas of known concentration provided from a compressed gas cylinder can be used for gas chromatograph validation applications. Such an approach can be substantially more costly with a spectroscopic measurement. A reference gas measurement can involve gas flow rates through a sample measurement cell at rates of, for example, approximately 0.1 to 3 liters per minute, which is multiple orders of magnitude greater than the typical flow rates of micro-liters per minute used in gas chromatographs. Reference gas blends provided in compressed gas cylinders can be difficult or impossible to obtain, especially in remote areas of the world where many natural gas processing, petrochemical, chemical, and refining plants are located. Shipping of pressurized gas cylinders can be costly and can take a very long time because pressurized gas cylinders generally cannot be shipped on airplanes. Additionally, reference gas cylinders can require heating blankets or placement inside temperature controlled cabinets, housings, etc. to prevent diurnal temperature fluctuations from rapidly degrading the certified reference composition in the cylinder. In addition carrier gas and trace analytes have been found to not mix uniformly, e.g. at typical gas cylinder pressures of 50 psi (pounds per square inch) to 3000 psi, without mechanical agitation or heating. As a result, even a reference gas mixture that is gravimetrically certified upon original preparation (e.g. by use of suitable bureau of standards traceable weights and scales) can produce varying trace gas concentrations in the gas withdrawn from the cylinder over time, thereby creating erroneous, changing concentration readings of the analyzer during successive validation attempts.

Even with such precautions, however, a pressurized cylinder containing a reactive trace gas will typically maintain a stable, reproducible reference gas concentration for only a few months at most, due to reactions of the trace gas with the cylinder. Reactions with cylinder walls can be a significant issue for many reactive trace gases, including but not necessarily limited to $H_2S$, $HCl$, $NH_3$, $H_2O$, and the like. It can be especially difficult to prepare accurate moisture blends that remain stable for a period longer than 6 months. At present, certified and traceable reference gas blend in pressurized cylinders that reliably provides a moisture content of less than about 10 ppm with an accuracy better than approximately ±10% are not available. Thus, instrument validations for analyzers capable of measuring moisture levels of less than about 1 ppm, for example in liquefied natural gas, dry cracked gas, hydrogen, nitrogen, oxygen, air, ethylene, propylene, olefins propane and butanes, can be extremely difficult. As an example, this lack of a suitable moisture reference gas mix for concentrations <10 ppm currently presents a very significant operational challenge for production of liquid gas. Typically, natural gas liquefication trains need to reliably maintain moisture levels well below 1.5 ppm to mitigate icing of the liquefication equipment. Undetected moisture excursions to levels above about 1 ppm generally lead to icing of the equipment. A single instance of needing to thaw the gas liquefication equipment to restore productive operations can readily result in an operating loss in excess of $5,000,000.

Production of ethylene and propylene, the basic building blocks for the vast majority of plastics used in daily life, carries requirements to maintain trace impurity levels well below 50 ppb to prevent production of inferior quality polyethylene and poly-propylene. These impurities can include, but are not limited to, $NH_3$, $H_2O$, $C_2H_2$, $CO_2$ and CO. In general, bottled gas mixtures cannot provide accurate, bureau of standards traceable validation for such low concentration measurements. Permeation tube validation technology is not well suited to providing trustworthy validation results for ethylene and propylene contamination measurements either. In addition to the extreme requirements for temperature stability and flow control, permeation tube devices are generally incapable of reliably providing trace gas concentrations below 10 ppm. Typical optical and TDL trace gas analyzers that measure below 50 ppb cannot support accurate measurement of trace gas levels greater than approximately 10 ppm at the same time.

SUMMARY

In one aspect, an apparatus includes a validation cell positioned such that light generated by a light source passes through the validation cell at least once in transmission of the light from the light source to a detector. The validation cell contains a reference gas that includes a known amount of a target analyte. A flow switching apparatus directs a sample gas into a path of the light during a sample analysis mode and a zero gas into the path of the light during a validation mode. The zero gas has at least one of known and negligible first light absorbance characteristics within a range of wavelengths produced by the light source. The apparatus also includes a controller performs operations that include receiving light intensity data quantifying intensity of the light received at the detector during the validation mode, comparing the light intensity data with a stored data set representing at least one previous measurement in the validation mode, determining that a validation failure has occurred if the first light intensity data and the stored data set are out of agreement by more than a predefined threshold amount.

In an interrelated aspect, a method includes receiving light intensity data quantifying intensity of light generated by a light source and received at a detector during a validation mode of an absorption spectrometer. The validation mode includes causing the light to pass at least once through each of a zero gas and a reference gas that is contained within a validation cell and that includes a known amount of a target analyte. The zero gas has at least one of known and negligible first light absorbance characteristics within a range of wavelengths produced by the light source. The method also includes comparing the light intensity data with a stored data set representing at least one previous measurement in the validation mode, and determining that a validation failure has occurred if the first light intensity data and the stored data set are out of agreement by more than a predefined threshold amount.

In additional aspects, articles are also described that comprise a tangibly embodied machine-readable medium operable to cause one or more machines (e.g., computers, etc.) to result in operations described herein. Similarly, computer systems are also described that may include a processor and a memory coupled to the processor. The memory may include one or more programs that cause the processor to perform one or more of the operations described herein.

In some variations one or more of the following additional features can optionally be included in any feasible combination. The light intensity data can include first light intensity data quantifying the intensity of the light received at the detector during a first phase of the validation mode in which the validation cell is maintained at a first temperature and second light intensity data of the light received at the detector during a second phase of the validation mode in which the validation cell is maintained at a second temperature that differs from the first temperature. The determining that the validation failure has occurred can include identifying that a first line shape of the first light intensity data and a second line shape of the second light intensity data deviate from a stored data set by a first deviation amount that exceeds a pre-defined threshold amount. The stored data set can include one or more previously recorded line shapes at the first temperature and the second temperature.

The additional optional features can also include promoting an alert that the validation failure has occurred, for example by the controller of the apparatus. A temperature control apparatus can be included to maintain the validation cell at least at one of the first temperature and the second temperature. A sample measurement cell can be included to contain an analysis volume. The sample measurement cell can be positioned such that the light passes at least once through each of the analysis volume in the sample measurement cell and the reference gas in the validation cell during transmission of the light from the light source to the detector. An optical cell can in include both of the validation cell and the sample measurement cell.

The additional optional features can also include making a first modification to at least one operating parameter of the light source, the detector, and the controller in response to the determining that the validation failure has occurred. New light intensity data can be received representing the light received at the detector during a repeated validation mode occurring after the first modification of the at least one operating parameter. The new light intensity data can be compared with the stored data set. A determination can be made whether the new light intensity data and the stored data set are out of agreement by more than the predefined threshold amount, and if so, whether the new light intensity data and the stored data set are in closer agreement than the light intensity data and the stored data set.

The additional optional features can also include the light source including a tunable or scannable laser of a laser absorption spectrometer. The stored data set can include a reference harmonic absorption curve of the laser absorption spectrometer, having a reference curve shape and including at least one of a first or higher order harmonic signal of a reference signal generated by the detector in response to light passing from the light source through the reference gas in the validation cell. The reference harmonic absorption curve can have been determined for the laser absorption spectrometer in a known or calibrated state. The light intensity data can include a test harmonic absorption curve having a test curve shape. The predefined threshold amount can include a predefined allowed deviation between the test curve shape and the reference curve shape. One or more operating and/or analytical parameters of the laser absorption spectrometer can be adjusted to correct the test curve shape to reduce the difference between the test curve shape and the reference curve shape. The one or more operating and/or analytical parameters of the laser absorption spectrometer can include one or more of laser light source parameters, detector parameters, and signal conversion parameters used in generating the test harmonic absorption curve from a signal produced by the detector.

The additional optional features can also include promoting a field validation metric of the laser absorption spectrometer. The field validation metric can include at least one of the difference between the test curve shape and the reference curve shape an identification of the one or more operating and analytical parameters that were adjusted, and a value by which the one or more operating and analytical parameters were adjusted. The laser light source parameters can include at least one of a temperature, an operating current, a modulation current, a ramp current, a ramp current curve shape, and a phase of the laser light source. The detector parameters can include at least one of a gain and a phase setting of a detector circuit. The signal conversion parameters can include at least one of a gain and a phase setting of the demodulating device.

The additional optional features can also include applying, as part of the comparing, a curve fitting algorithm to quantify the difference between the test curve shape and the reference curve shape. The comparing can also or alternatively further include applying at least one of subtracting, dividing, cross correlation, curve fitting, and multivariable regression for one or more parts or the entire of the test curve and the reference curve, and computing one or more of the difference, the ratio, the mean square error (MSE), the coefficient of determination ($R^2$), the cross correlation function/integral and the regression coefficients in the light intensity (i.e., the y-axis) and/or the wavelength (i.e. the x-axis) domain to quantify the difference between the test curve shape and the reference curve shape. The reference harmonic absorption curve can include at least one of a calibration reference curve stored during calibration of the laser absorption spectrometer and a constructed curve comprising one or more mathematically combined stored calibration reference curves selected according to at least one of a composition of a background gas that the sample gas comprises and an expected concentration of a target analyte to be measured in the sample gas containing the background gas.

The subject matter described herein provides many advantages. For example, validation of an existing calibration of a gas analyzer can be performed with lower cost, less complexity, and the need only to supply a zero gas (described in more detail below) in the sample measurement cell (or alternatively in a free gas space that contains a sample gas during an analysis mode) to provide an absorbance-free background for a validation measurement. Nitrogen, an example of a zero gas, can be especially easy to obtain, for example in compressed cylinders, from an on-site air separation plant that manufactures nitrogen from air, or the like. Use of a stable, easy to obtain zero gas can eliminate shelf life issues typically associated with compressed gas cylinders containing mixes of the trace gas itself and can also eliminate issues related to gas mixing at high pressures and withdrawal of gas mixes from compressed cylinders.

Furthermore, the current subject matter can eliminate or at least reduce the need for costly and complex permeation tube devices and/or for reference gases in pressurized gas cylinders, which can be difficult to obtain and maintain. Repeated measurement validation checks can be performed over long periods of time without significant aging effects and without consuming a difficult to obtain and shelf life limited reference gas mixture.

The current subject matter can also enable an absorption spectrometer to re-calibrate itself or example using an iterative process in which one or more operating and/or analytical parameters of the laser absorption spectrometer are adjusted to find new operating and/or analytical conditions that cause the spectrometer to perform more closely to a previously recorded calibration condition.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
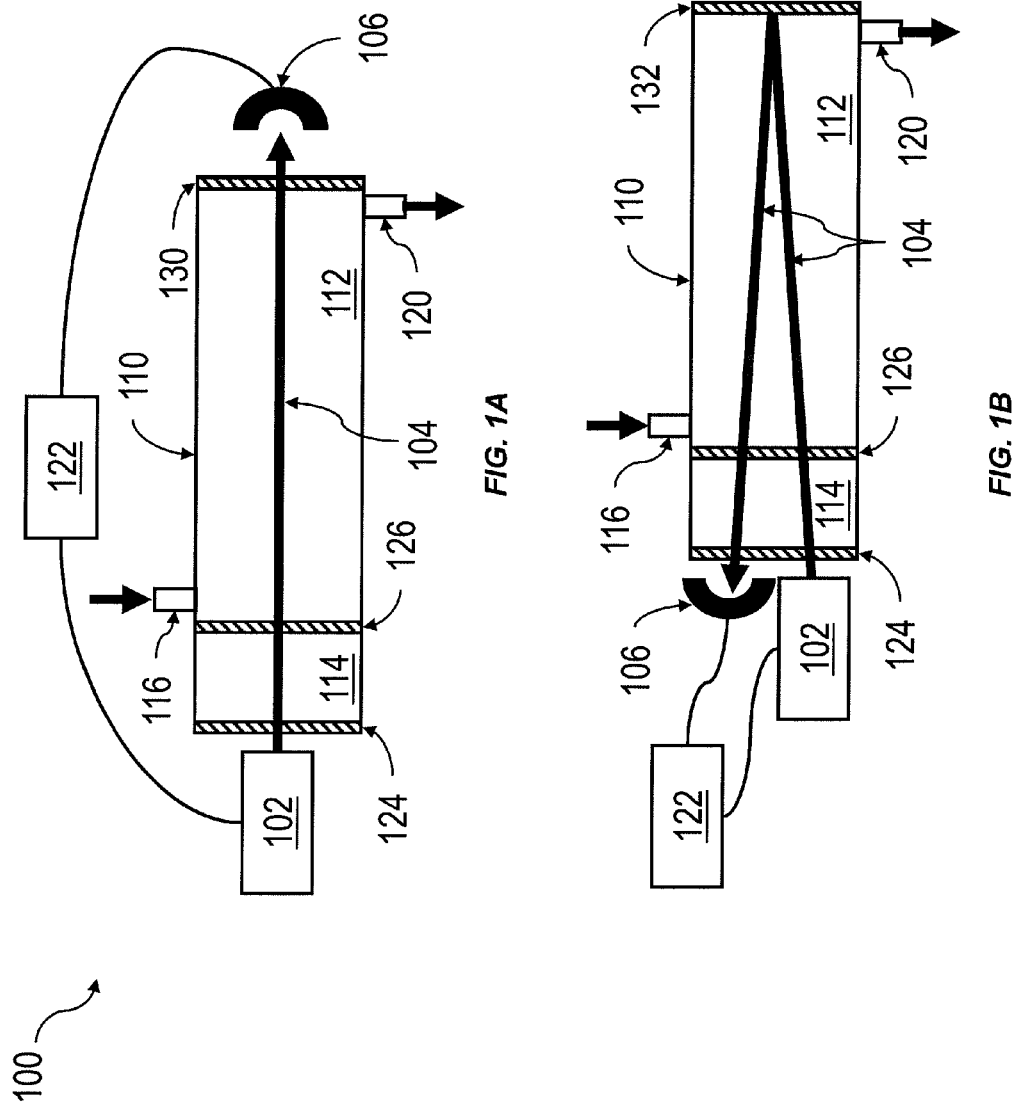
FIG. 1A and FIG. 1B show examples of sample measurement cells including a sample volume and a validation cell.

To address the above noted and potentially other issues with currently available solutions, one or more implementations of the current subject matter provide methods, systems, articles of manufacture, and the like that can, among other possible advantages, provide an integrated measurement fidelity validation capability into an optical absorption cell of a spectrometer. The only gas needed for field validation is a suitable, easy to obtain, cost effective, zero gas. As used herein, the term "zero gas" refers to the contents of a sample measurement cell that have a negligible, or alternatively a well-characterized, absorbance of light overlapping a target spectral feature of one or more target analytes to be detected in a sample gas mixture. An in-line validation cell contains a reference gas, and is positioned such that light from a light source passes through both of the validation cell and the sample measurement cell on its way to a detector that quantifies a received light intensity. Such an arrangement can eliminate the need for complicated and expensive devices to tightly control temperature and flow as is required for instrument validation when using permeation devices or dilution of pre-mixed trace gas blends from compressed gas cylinders. The zero gas can be, for example, noble gases, nitrogen gas ($N_2$), hydrogen gas ($H_2$), oxygen gas ($O_2$), any homo-nuclear diatomic gas, any gas which has negligible absorption at the chosen wavelength of the trace analyte measurement of interest, any gas which does not contain the trace analyte of interest at levels detectable by the instrument, vacuum, or the like. Such a zero gas can be further conditioned by removing any potential trace gas contamination through use of a suitable filter or scrubber, to levels below the detection limit of the analyzer. Filters reducing total hydrocarbons, moisture, $CO_2$, CO and other contaminants to low single digit ppb levels, or lower can be used in some implementations. Chemically reactive scrubbers that reduce the trace analyte concentration to below the instrument's detection level can be used in some implementations. Examples of such scrubbers are described in co-owned U.S. Pat. No. 7,829,046. Driers reducing the total moisture concentration to levels below the instrument detection limit can be used in some implementations. The zero gas can, in some implementations, be a vacuum, or alternatively, a gas mixture having a known composition with a well-characterized spectral response at the wavelength or wavelengths of interest for a spectroscopic analysis.

Implementations of the current subject matter can provide improved fidelity between a validation measurement and a sample measurement by placing the validation cell in line with the sample measurement cell. This configuration allows measurement of the trace gas concentration in the sample measurement cell and in the validation cell simultaneously, as the sum of trace gas concentrations in the sample measurement cell and the validation cell. In this novel optical arrangement for quantitative trace gas spectroscopy, a single optical measurement beam interacts spatially and temporally with an unchanging gas volume, the same optically reflective and transmissive surfaces, and the same detector whenever it measures a trace gas concentration or a zero gas concentration in the sample measurement cell while simultaneously passing through the trace gas concentration in the validation cell.

A suitable data algorithm can compare one or more stored reference spectral scans collected with zero gas in the sample measurement cell (thereby reflecting absorbance of only the reference gas in the validation cell) with a measured composite trace gas scan collected with a sample gas in the sample measurement cell (thereby reflecting absorbance of gases in both the sample measurement cell and the validation cell) to derive the trace gas concentration in the sample measurement cell. Comparing the zero gas validation cell reading and spectral traces with one or more electronically stored reference spectral traces collected during instrument calibration can be used to validate the fidelity of the measurement of the sample gas.

Additionally, analyzing the validation cell spectral traces and concentration measurement without an absorbing gas in the sample measurement cell allows for automatic reconstruction of a calibration state of the instrument, for example as described in co-pending and co-owned provisional application Ser. No. 61/405,589. In contrast, previously available approaches employing a validation cell that is outside of the measurement beam path and/or that uses a separate detector and separate optical components can lead to different and difficult to quantify factors influencing one or more components of the two separate analytical units. For example, characteristics of the validation cell and measurement cell, reference detector and measurement detector, or one or more of the optical components serving either of the reference or sample analytical paths, etc. can vary independently over time. The current subject matter can also provide advantages in reducing the number of optical surfaces that can degrade the signal to noise ratio and detection sensitivity of an instrument.

FIG. 1A and FIG. 1B depict examples of spectroscopic gas analyzers 100 and 101 illustrating features consistent with at least some implementations of the current subject matter. A light source 102 provides a continuous or pulsed beam of light 104 that is directed to a detector 106. The beam of light 104 passes through a sample measurement cell 112 that includes a sample volume and a segregated, sealed validation cell 114 that contains a static, known amount of a reference gas. The validation cell 114 can be maintained at a stable temperature to maintain a stable gas pressure of the reference gas in the fixed volume validation cell 114. In a further implementation, the temperature of the reference gas in the validation cell 114 can be measured to compute the pressure in the validation cell 114 by application of the ideal gas law, $$PV = nRT \tag{1}$$

where P is the pressure within the validation cell 114, V is the (known and constant) volume of the validation cell 114, T is the measured temperature in the validation cell 114, n is the (known) number of moles of the reference gas in the validation cell 114, and R is the gas constant (8.314472 J·mol$^{-1}$·K$^{-1}$).

The measured temperature and derived pressure inside the validation cell 114 can be used to numerically correct the trace gas spectrum in the validation cell 114 with respect to a previously measured and stored calibration state. This numerical correction can be accomplished by comparing a spectral trace measured with zero gas in the sample measurement cell 112 with a previously stored reference spectral trace and the respective measured temperature and derived pressure that are stored in an electronic medium at the time of calibration.

Throughout this disclosure, the term "validation cell" is used to refer to a sealed volume containing a known quantity of at least one target analyte. It can alternatively be referred to as a reference gas reservoir or reference gas volume. The light source 102 can include, for example, one or more of a tunable diode laser, a tunable semiconductor laser, a quantum cascade laser, a vertical cavity surface emitting laser (VCSEL), a horizontal cavity surface emitting laser (HCSEL), a distributed feedback laser, a light emitting diode (LED), a superluminescent diode, an amplified spontaneous emission (ASE) source, a gas discharge laser, a liquid laser, a solid state laser, a fiber laser, a color center laser, an incandescent lamp, a discharge lamp, a thermal emitter, and the like. The detector 106 can include, for example, one or more of an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (PbSe) detector, a thermopile detector, a multi-element array detector, a single element detector, a photo-multiplier, and the like.

The sample measurement cell 112 can include a gas inlet 116 and a gas outlet 120 through which a sample of gas to be analyzed can be passed into and out of the sample volume, respectively. A controller 122, which can include one or more programmable processors or the like, can communicate with one or more of the light source 102 and the detector 106 for controlling the emission of the beam of light 104 and receiving signals generated by the detector 106 that are representative of the intensity of light impinging on the detector 106 as a function of wavelength. In various implementations, the controller 122 can be a single unit that performs both of controlling the light source 102 and receiving signals from the detector 106, or it can be more than one unit across which these functions are divided. Communications between the controller 122 or controllers and the light source 102 and detector 106 can be over wired communications links, wireless communications links, or any combination thereof.

The sample measurement cell 112 can also include at least one optical feature for transmitting and/or reflecting the beam of light 104 between the light source 102 and the detector 106. Such optical components can advantageously have a low absorbance of light at the wavelength or range of wavelengths at which the light source 102 emits the beam of light 104. In other words, a reflective optical component would advantageously reflect more than 50% of the incident light at the wavelength or in the range of wavelengths, in a single reflection, an optical light guide would advantageously transmit more than 2% of the incident light, and a window would advantageously be anti-reflection coated and transmit more than 95% of the incident light at the wavelength or in the range of wavelengths. In the example configuration illustrated in FIG. 1A, the beam of light 104 first passes through a first window 124 to enter the validation cell 114, a second window 126 to enter the sample volume of the sample measurement cell 112, and a third window 130 to reach the detector 106. Other configurations are within the scope of the current subject matter. For example, as shown in FIG. 1B, instead of the third window 130 that is shown in FIG. 1A, a mirror 132 can reflect the beam of light 104 back through the sample volume of the sample measurement cell 112 and the validation cell 114 while also passing a second time through the second window 126 and the first window 124. Other possible configurations include the first window 124 being formed as part of a larger mirror that causes the beam of light 104 to reflect multiple times through the sample volume of the sample measurement cell 112 and the validation cell 114 before impinging upon the detector 106.

Figure 2:
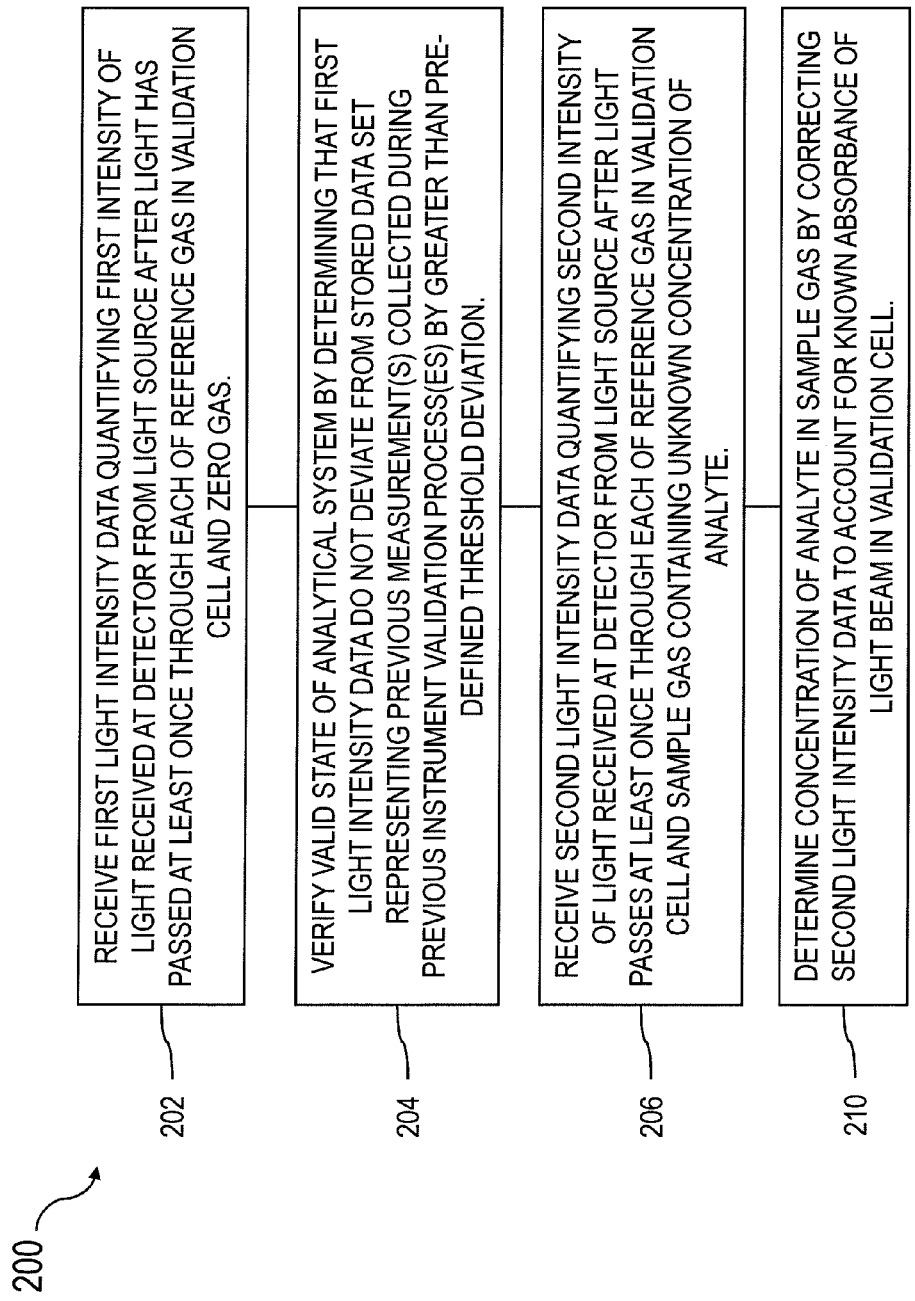
FIG. 2 is a process flow diagram illustrating aspects of a method consistent with implementations of the current subject matter.

FIG. 2 shows a process flow chart 200 illustrating features of a method consistent with at least one implementation of the current subject matter. At 202, first light intensity data are received. The first light intensity data quantify a first intensity of light received at a detector 106 from a light source 102 after the light, which can be a light beam 104, has passed at least once through each of a reference gas in a validation cell 114 and a zero gas. The reference gas includes a known amount of an analyte compound. The light source 102 emitting the light in a wavelength range that comprises a spectral absorbance feature of the analyte compound. The zero gas can, as noted above, be a gas or gas mixture or a complete or partial vacuum having at least one of known and negligible first light absorbance characteristics that overlap second light absorbance characteristics of a trace analyte within a range of wavelengths produced by the light source. The zero gas can also include a spectrally absorbing gas having well known absorption characteristics that have been characterized and stored in an electronic medium in retrievable format, in the measured wavelength region. At 204, a valid state of the analytical system is verified by determining that the first light intensity data do not deviate from a stored data set by greater than a pre-defined threshold deviation. The stored data set represent at least one previous measurement collected during a previous instrument validation process of the analytical system that includes at least the light source 102 and the detector 106. Second light intensity data are received at 206. The second light intensity data quantify a second intensity of the light received at the detector from the light source after the light passes at least once through each of the reference gas in the validation cell and a sample gas containing an unknown concentration of the analyte. At 210, a concentration of the analyte compound in the sample gas is determined by correcting the second light intensity data to account for a known absorbance of the light in the validation cell. In some implementations, the correcting can include subtracting a reference spectrum generated based on first intensity data from a validation mode data set from a sample spectrum generated during the sample analysis mode.

A sample gas can be directed into a path 104 of the light during a sample analysis mode and a zero gas can be directed into the path 104 of the light during a validation mode. The sample gas and zero gas can be directed into the analysis volume of the sample measurement cell 112, for example using a flow switching apparatus that can in various implementations include one or more valves, flow controllers, vacuum pumps, or the like that can be controlled to provide a desired gas in the beam path of the light from the light source 102. A controller 122 that comprises a programmable processor can receive the first light intensity data and the second light intensity data and can perform the verifying of the valid state. The stored data set can be used by the controller for automated recovery of the original calibration state of the spectrometer, for example as described in co-pending and co-owned provisional application Ser. No. 61/405,589, which has been incorporated herein by reference and in greater detail below.

Figure 3:
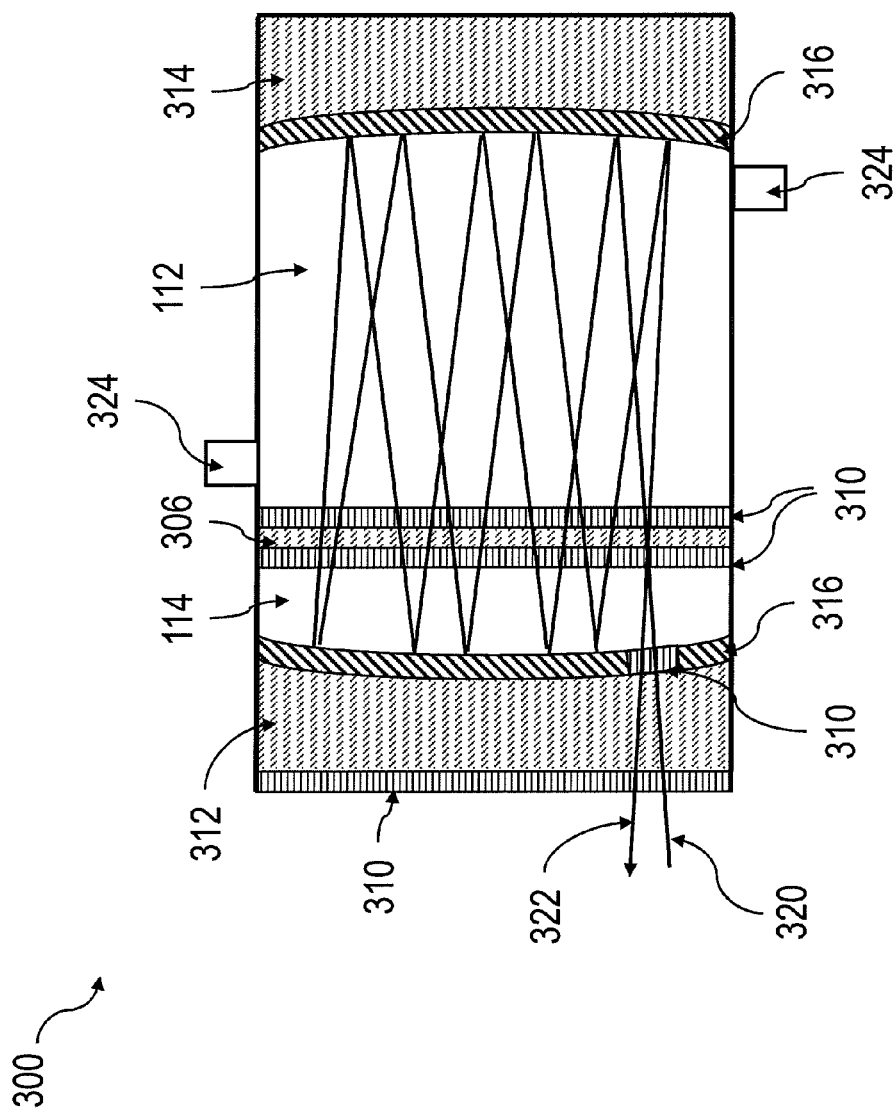
FIG. 3 is a diagram showing an example of a sample measurement cell configured for multiple passes of a light beam through a validation cell and a sample volume.

FIG. 3 is a diagram of an optical cell 300 that is consistent with one or more implementations of the current subject matter. The optical cell 300 includes a validation cell 114 and a sample volume of a sample measurement cell 112. A barrier 306 formed of an optically transparent material can divide the validation cell 114 and the sample measurement cell 112 portions of the optical cell 300. The barrier 306 can be optically coated on both sides with an anti-reflective coating 310 of single or multi-layer material, that can be made from oxides, such as for example $SiO_2$, $TiO_2$, $Al_2O_3$, $HfO_2$, $ZrO_2$, $Sc_2O_3$, $NbO_2$ and $Ta_2O_5$; fluorides, such as for example $MgF_2$, $LaF_3$, and $AlF_3$; etc. and/or combinations thereof. The optical antireflection coating can be deposited by a technique such as for example electron beam evaporation, ion assisted deposition, ion beam sputtering, and the like. The optical cell 300 can be contained between a first reflector 312 and a second reflector 314, each of which can have a curved surface and/or a flat surface that includes a coating of a highly reflective material 316, such as for example metallic materials (e.g. Au, Ag, Cu, steel, Al, and the like), one or more layers of transparent dielectric optical materials (e.g. oxides, fluorides, etc.), and/or a combination of metallic and dielectric optical materials. The reflectors can optionally be made entirely of dielectric materials, without any metal reflector. The first reflector 312 can include an outer coating of the anti-reflective material 310 as well as at least a gap or opening in the coating of the highly reflective material 316 that can be coated with the anti-reflective material 310 so that an incoming beam 320 of light can pass into the optical cell 300 in the space between the first reflector 312 and the second reflector 314. The incoming beam 320 can be generated by a light source (not shown in FIG. 3).

After entering the optical cell, the incoming beam 320 of light can be reflected a plurality of times between the first reflector 312 and the second reflector 314 before exiting the optical cell 300 as an outgoing beam of light 322, optionally through the same area of the coating of anti-reflective material 310 on the inner surface of the first reflector 312. In this manner, the beam of light passes multiple times through the sample measurement cell 112 as well as through the validation cell 114. A sample gas can be admitted into the sample measurement cell 112, optionally via a sample inlet 324, and removed from the sample measurement cell 112, optionally via a sample outlet 326. One or more valves or other flow controlling devices can be coupled to the sample inlet 324 to switch between flow of a sample gas and a zero gas into the sample measurement cell 112. The sample gas can be admitted to the sample volume of the sample measurement cell 112 for measurements in a sample analysis mode and the zero gas can be admitted to the sample volume of the sample measurement cell 112 for measurements in a validation mode. It should be noted that the optical cell 300 is merely an example configuration. Other configurations of the optical cell 300 are also within the scope of the current subject matter. For example, the first reflector 312 and the second reflector 314 can be positioned opposite one another with a free gas space between them. The validation cell 114 can be positioned as shown in FIG. 3. With such a configuration, the concentration of one or more analytes in the gas occupying the free gas space can be analyzed in a similar manner as described herein.

In some implementations, a metal alloy, such as for example AL 4750™ (available from Allegheny Ludlum of Pittsburgh, Pa.), can be used as a spacer between the windows and mirrors, which can be made in some examples of BK-7™ optical glass (available from Esco Products of Oak Ridge, N.J.). It can be advantageous to choose window and spacer materials that have similar thermal expansion characteristics. In some implementations, mirror and window materials can be attached to spacer material by glass fitting, soldering, or some other technique capable of forming a very low permeation ultra-high vacuum seal that can, for example, maintain a leak rate for He (helium) of less than approximately $10^{-6}$ standard torr·cm$^3$·sec$^{-1}$.

Figure 4:
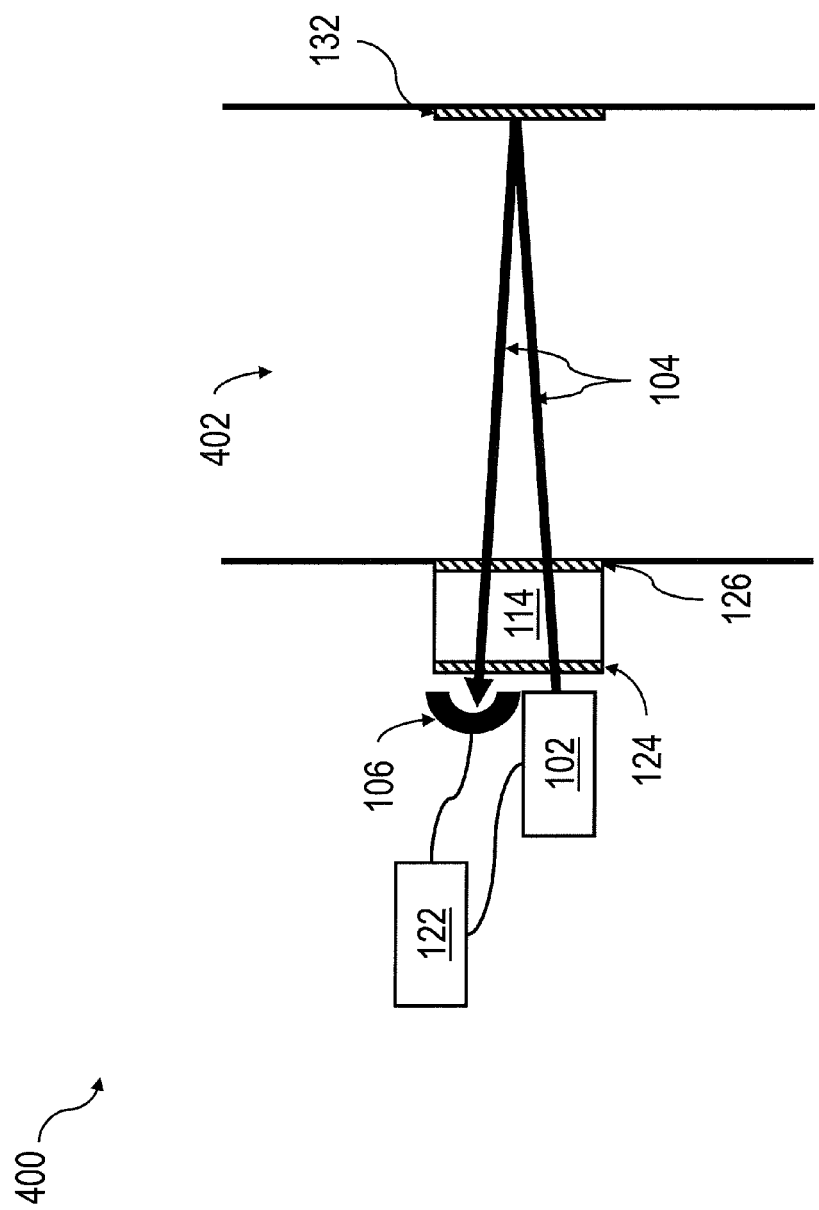
FIG. 4 is a diagram showing an example of an analytical system including a free gas space.

As noted above, other configurations of an analytical system are also within the scope of the current subject matter. For example, as illustrated in the example of an open path analytical system 400 shown in FIG. 4, the sample gas and the zero gas need not be contained within a sample volume within an optical cell or a sample measurement cell. Such an open path analytical system 400 can include a validation cell 114 that contains a sealed volume including a known amount of one or more target analytes. The validation cell 114 can be positioned such that a beam of light 104 from a light source 102 passes at least once through the validation cell 114 on its way to a detector 106. The path of the light traverses a free gas space 402 or other volume that need not be constrained within a container. The free gas space can at least occasionally experience passage of a sample gas containing the target analyte. For example, the path of the light can traverse an exhaust stack or other open flow path of a refinery, power plant, factory, or the like. The light also passes through the validation cell 114 before reaching the detector 106 that quantifies light intensity, for example as a function of wavelength, of the light. A validation mode can include diverting the process gas from the free gas space 402 and replacing with a zero gas.

Figure 5:
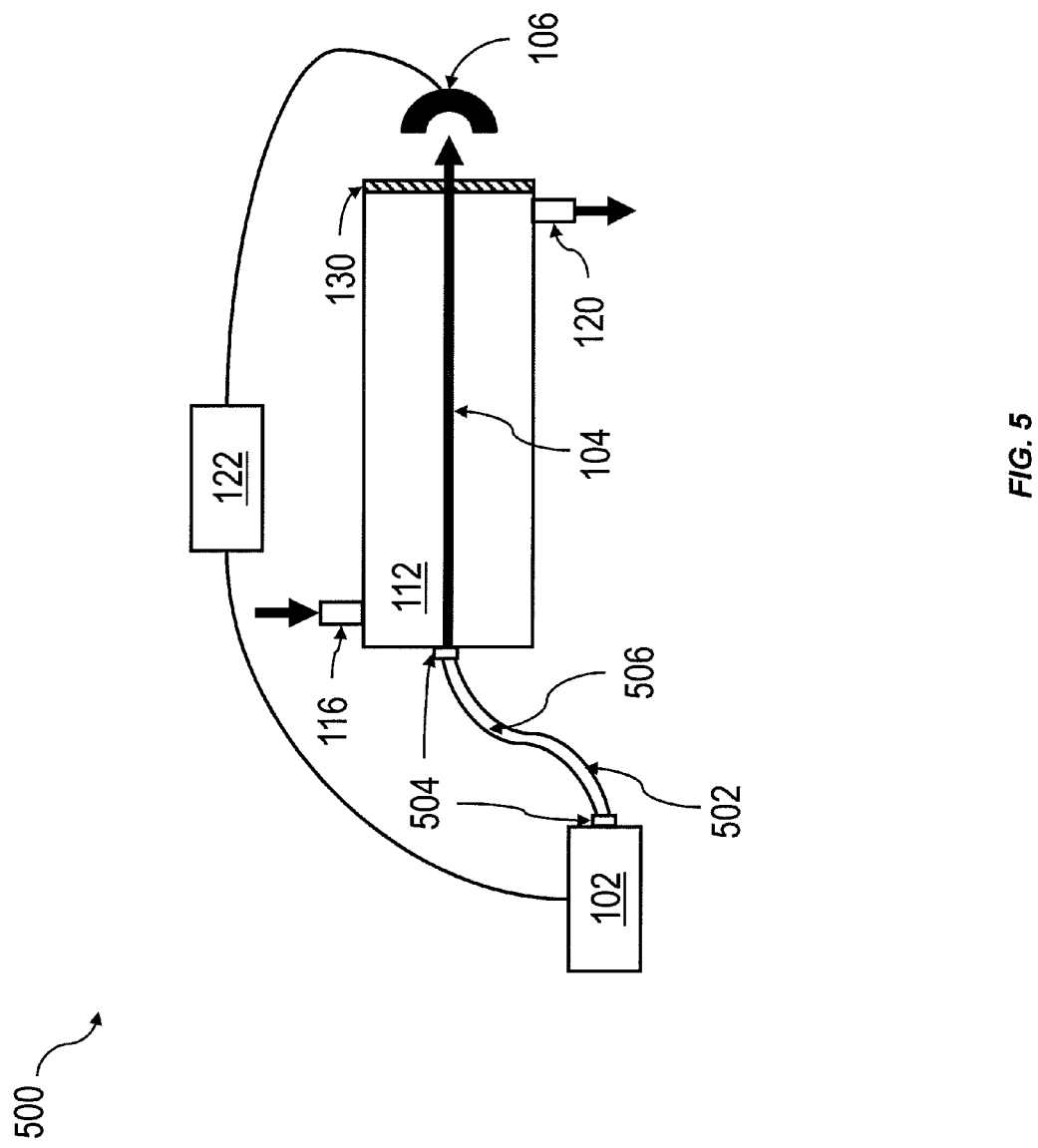
FIG. 5 is a diagram showing an example of a hollow core optical light guide configured as a validation cell.

In some implementations, for example in the example system 500 shown in FIG. 5, a hollow core optical light guide 502 can be vacuum sealed with one or more sealing optical elements 504 that can include, but are not limited to, flat components, curved components, diffractive components, and the like. The sealing optical elements 504 can, in some implementations, transmit at least 95% of the incident light directed into the light guide 502 and at least 95% of the light transmitted by the light guide 502 back out of it. The sealed hollow core 506 of the optical light guide 502 can contain a reference gas as described elsewhere herein and thereby serve as a validation cell 114 through which light from the light source 102 passes before reaching the sample measurement cell 112. The sealing optical elements 504, which can include but are not limited to antireflection-coated optical windows, light transmissive optical surfaces, and the like that provide a means for light to enter and exit the sealed hollow core 506 of the hollow core optical light guide 502 while also optionally forming a leak tight gas seal between the sample stream and the outside world, can collimate light emitted from a laser light source 102 into the optical light guide 502 and collimate the light exiting the optical light guide 502 into the sample measurement cell 112, such as for example one of the variations discussed herein or an equivalent.

The validation cell 114 within the hollow core 506 of the light guide 502 can alternatively be used with non attached optical elements focusing the laser light into it and non attached optical focusing elements that focus the fiber transmitted light into the sample measurement cell 112, or a combination of attached and non attached optical elements. The optical focusing elements can optionally form all or part of a leak tight gas seal between the hollow core optical light guide 502 and the outside world. A hollow core optical light guide 502 can be constructed from one or more materials that can include but are not limited to metal, glass, plastics, polytetrafluoroethylene (e.g. Teflon™ available from DuPont of Wilmington, Del.), Tygon (available from the Saint Gobain Corporation of Courbevois, France), and the like, which can be used individually or in combination.

Figure 6:
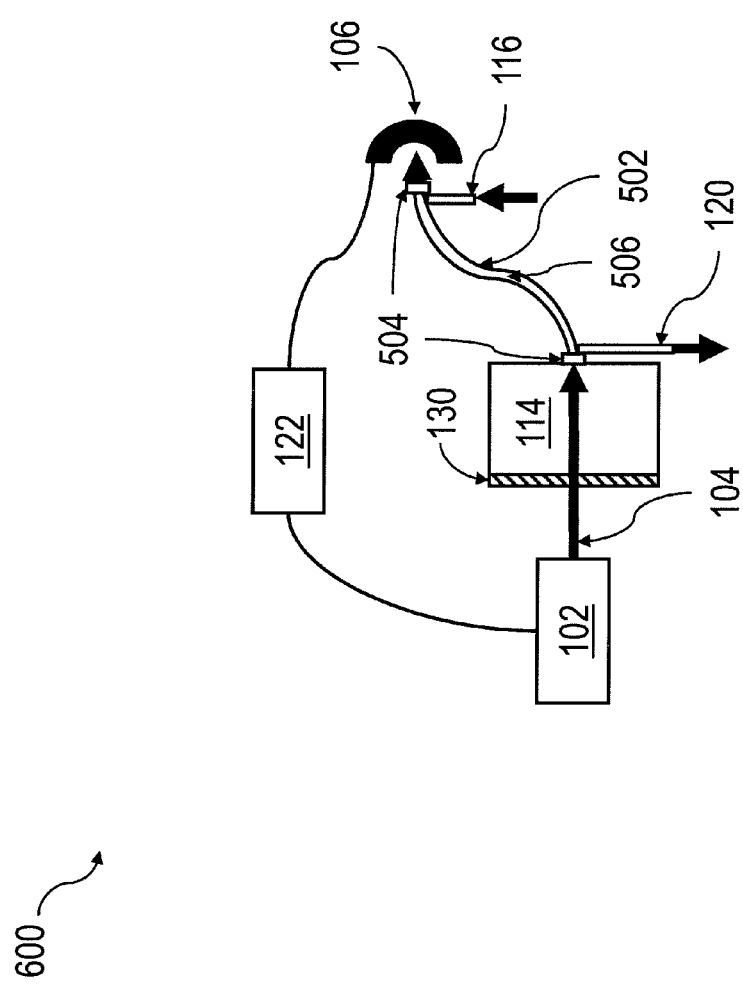
FIG. 6 is a diagram showing an example of a hollow core optical light guide configured as a validation cell.

A hollow core optical light guide 502 can alternatively or in addition be used as a sample measurement cell 112, for example in the system 600 illustrated in FIG. 6. In the implementation illustrated in FIG. 4, the hollow core optical light guide 502 can have a gas inlet 116 and a gas outlet 120, each hermetically sealed to the outside of the hollow core optical light guide 502 to allow sample gas or zero gas to be provided into the sealed hollow core 506 of the optical light guide. Light can be passed into the hollow core optical light guide 502 by means of a suitable optical focusing arrangement of the beam provided by a light source 102. Light travels through the hollow core optical light guide 502 containing the sample gas, in a single direction. The light source 102 and the detector 106 can be positioned at either end of the hollow core optical light guide 502. In some implementations, a hollow core optical light guide 502 as described herein (e.g. for either or both of a validation cell 114 and a sample measurement cell 112) can have an internal open core dimension perpendicular to the light beam 104 smaller than 3.5 mm and an internal open core dimension parallel to the light beam 104 greater than 0.1 mm.

In another implementation, both of the validation cell 114 and the sample measurement cell 112 can be contained within separate hollow core light guides that are optically and, optionally, physically coupled to one another such that light passes through both a first hollow core light guide containing the validation cell 114 and a second hollow core light guide 502 containing the sample measurement cell 112.

In other implementations, the light source 102 can be a hermetically sealed laser package, such as for example a butterfly package or a TOSA package commonly used for telecommunications lasers. A hollow core optical light guide 502 can be hermetically sealed to the hermetic laser package of the light source 102 with the hollow core 506 open to the interior of the hermetic laser package such that the hollow core 506 of the light guide 502 and the hermetic laser package form a sealed volume within which a reference gas as described elsewhere herein is contained to form a validation cell 114. In another variation, the hollow core optical light guide 502 can be hermetically sealed to the hermetic laser package with its hollow core sealed separately and filled with the reference gas similar to the configuration shown in FIG. 5 or provided with flow-through capability via and inlet port 116 and outlet port 120 to serve as a sample measurement cell 112 that can contain a sample gas or a reference gas as in FIG. 6.

Figure 7:
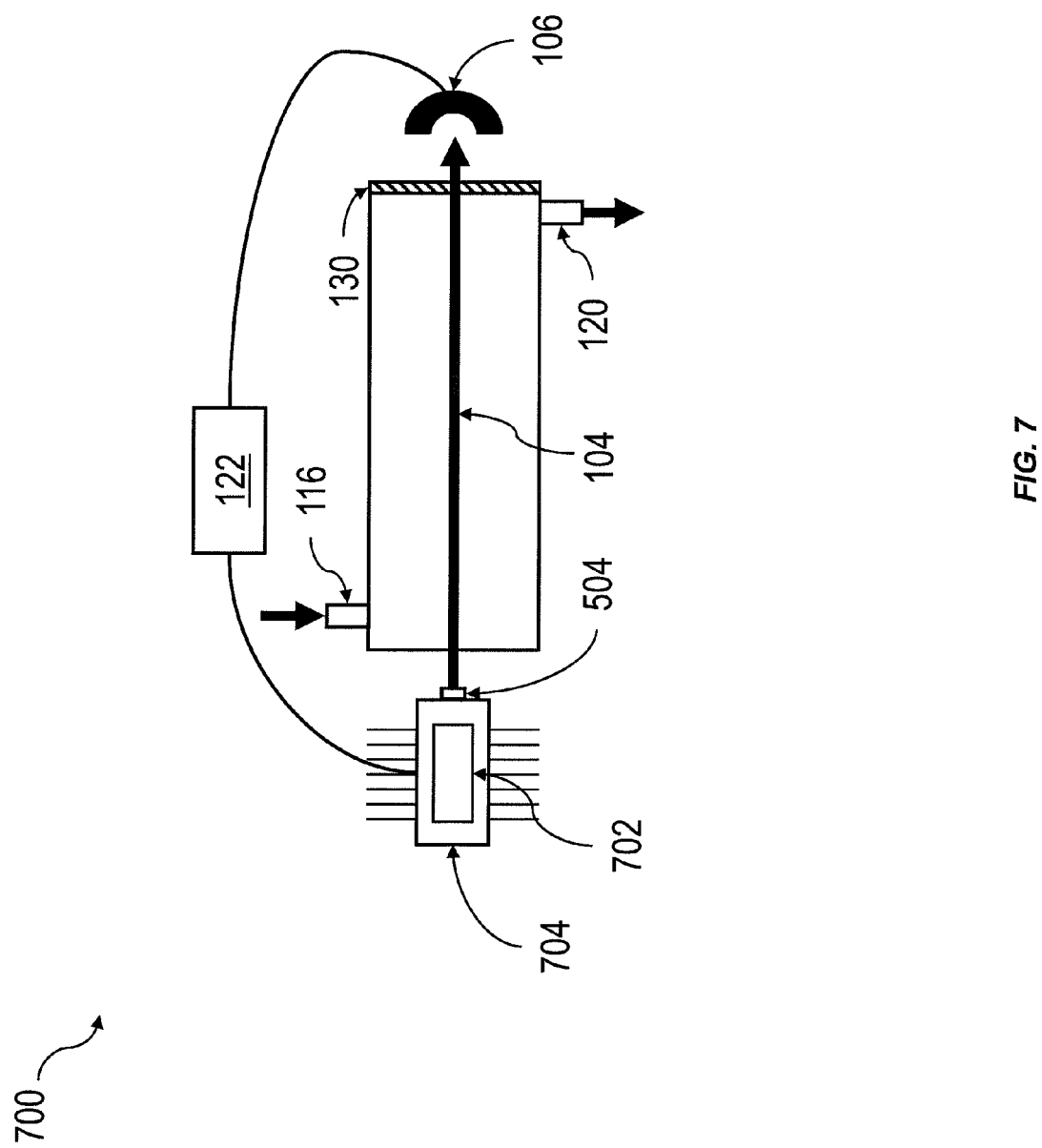
FIG. 7 is a diagram showing an example of a hermetically sealed laser package configured as a validation cell.

In another implementation, an example of which is illustrated by the system 700 of FIG. 7, a sealed volume 702 within a hermetically sealed laser package 704 can serve as both the light source and a reference gas reservoir that functions as the validation cell. The hermetically sealed volume 702 can be sealed by sealing optical elements 504 transmitting the laser light, for example into the sample measurement cell 112. The sealing optical elements can include, but are not limited to, flat, curved, fiber, refractive and diffractive components and combinations of these.

In at least some implementations, a validation cell 114 can be filled under precisely and accurately controlled temperature and pressure conditions, using a neat analyte or a well-known mole fraction of the analyte in a carrier gas mix. The reference gas can be filled into the validation cell 114, for example using a vacuum gas conditioning and filling station. The vacuum filling station can provide a heat out capability for the validation cell 114 to remove any unwanted moisture and other trace gases, before filling the validation cell 114 with a known amount of trace gas, and optionally some amount of carrier gas. The validation cell 114 can be attached to the vacuum pumping station by means of a single tube connection or by means of two tube connections enabling gas streaming through the validation cell 114. The validation cell 114 can be disconnected from a filling station that provides the reference gas mixture or neat analyte in a manner that creates a long lasting, ultra high vacuum seal, for example using a cold fusing pinch off operation. As used herein, the term neat refers to a preparation of the analyte without any diluting gas or other compound. For example, a neat preparation of water vapor in a validation cell 114 can be prepared by adding a known volume of liquid or gas phase water to an evacuated container.

An optical cell or measurement system, such as those described herein and/or functional equivalents thereto that includes an integrated gas cell, can permit preparation and long term stable preservation of an accurate reference sample of a neat analyte or a trace analyte that is present at a known mole fraction in a suitable background gas. In some implementations, such as for example when the reference gas sample in the validation cell 114 is prepared gravimetrically, the trace gas concentration in the validation cell 114 can be determined with respect to a NIST or other comparable traceable standard and/or certifications for a gas blend. The reference sample can be arranged directly in the measuring light beam 104 of a spectrometer. In some implementations of the current subject matter, an ultra-high-vacuum, leak-tight validation cell 114 can be placed in series with a sample measurement cell 112 of a spectrometer such that a small total amount of an analyte can be provided with no carrier gas. The reference sample can optionally include multiple analytes, for example if the spectrometer is configured for measurement of multiple analytes.

In both the sample analysis mode and the validation mode, the beam 104 of light from the light source 102 passes at least once through the validation cell 114 and interacts with all of the optical components of the analysis system before being detected and quantified by the detector 106. In the validation mode, the sample volume of the sample measurement cell 112 can be flushed or otherwise filled with an optically transparent gas that lacks a significant absorbance of light at a wavelength or in a range of wavelengths provided by the light source 102. Alternatively, the sample volume of the sample measurement cell 112 can be pumped to at least a partial vacuum condition such that little or advantageously no molecules of the analyte or any other species that significantly absorbs at the wavelength or in the range of wavelengths is present in the sample volume of the sample measurement cell 112. Thus, in the validation mode, the beam 104 of light experiences absorbance primarily by molecules of the analyte contained in the validation cell 114. This absorbance can be detected by the same detector 106 and under the same optical conditions as the absorbance for a gas sample in the sample measurement cell 112 when the spectrometer is operated in sample analysis mode. In the sample analysis mode, the sample volume of the sample measurement cell 112 contains a sample gas such that the beam 104 of light experiences absorbance by those molecules of the analyte contained in the validation cell 114 and those molecules of the analyte in the sample gas in the sample volume of the sample measurement cell 112.

An approach consistent with the currently described subject matter can ensure that the validation measurement will always include any and all aging and contamination related issues that can impact the actual measurement of analyte concentration in a sample gas in the sample volume. Use of a validation cell or other vessel or container for a reference gas that is not contained in the actual measurement beam path or that uses a different photo detector, different optical components, or the like may not as accurately characterize factors impacting the measurement of a sample gas are thus likely to give a less useful validation measurement of a spectrometer.

In at least some implementations, the light source 102, detector 106, and sample measurement cell can be part of a tunable diode laser (TDL) spectrometer or other spectrometer using a light source that is tunable to provide the beam of light with a narrow bandwidth wavelength that is scanned across a range of wavelengths. Alternatively, the light source 102, detector 106, and sample measurement cell can be part of an optical spectrometer using a broad band light source that provides the beam of light.

The controller 122 can, as noted above, receive signals from the detector 106 that are characteristic of the optical absorbance of the beam of light 104 as it passes between the light source 102 and the detector 106. In some implementations, an algorithm can include comparing a reference spectrum obtained during a validation mode measurement to an original reference gas calibration file for the instrument. An acceptable correlation fit between the factory calibration reference gas spectrum and the field obtained zero gas spectrum can indicate that no significant changes have occurred with the spectrometer and that measurement fidelity is maintained with respect to the original spectrometer factory calibration. In this way, validation of the analyzer calibration can be completed using only one gas for zeroing the absorbance due to a sample gas (for example in a sample volume). This approach simplifies field validation of an analyzer since only a single zero gas is used and because a suitable zero gas, such as $N_2$, which does not absorb in the infra red spectral region, can generally be very easy to obtain and store. The current subject matter can therefore dramatically improve on the typically used approach to field validation of analyzers in which validation of the zero reading is done using a suitable zero gas and validation of the span reading is done using a span gas blend provided by a pre-mixed cylinder.

Integrating the validation cell into the reflector for the trace gas measurement cell can improve spectrometer cell compactness, signal to noise ratio and detection sensitivity by reducing the number of optical surfaces compared to inserting a separate validation cell into the spectrometer beam path. Reducing the number of optical surfaces through which the light beam passes reduces potential for optical fringes, thus improving the spectrometer signal to noise ratio and detection sensitivity. Integrating the validation cell eliminates need for alignment of a separate validation cell and maintains relative alignment with respect to the measurement cell over time and all environmental conditions.

The reference trace gas concentration may be adjusted in the factory, as required for a specific application. Trace gas concentrations in the validation cell can be adjusted from 1 part per trillion (ppt) to 100%, as long as gas phase is being maintained under operating conditions. The operating temperature can be between −50 C to +200 C. The trace analyte may be stored in the validation cell at operating pressures between 1 mbar and 5000 mbar. The trace analyte may be neat or may be blended into suitable mixtures of carrier gases, which include but are not limited to $N_2$, $O_2$, air, $H_2$, $Cl_2$, other homo-nuclear diatomic gases, noble gases, $CO_2$, CO, hydrocarbon gases, hydrofluorocarbons (HFCs), chlorofluorocarbons (CFCs), fluorocarbons (FCs), and the like. Trace analytes can be any gas phase component that has an optical absorbance feature at a wavelength between about 100 nm and 20,000 nm. Analytes that can be quantified using one or more aspects of the current subject matter include but are not limited to $H_2O$, $H_2S$, $NH_3$, HCl, $C_2H_2$, $CO_2$, CO, $CH_4$, $C_2H_6$, $C_2H_4$, $O_2$, and the like.

Additional advantages of the current subject matter can include the ability to improve the robustness of laser frequency stabilization methods, for example from a tunable laser light source, which can lead to better tracking of target analyte absorbance peaks. For a sample gas stream that does not have a target analyte present at all times, it can be difficult to verify that the laser frequency is sufficiently stable to isolate the target absorbance peaks. In one illustrative example, a refinery or manufacturing process can be monitored for oxygen ($O_2$) concentration spikes for safety control. Oxygen may only be present in the stream under process upset conditions and in negligible amounts during normal process operation. If the laser light source of an instrument used for measuring oxygen to detect process upset conditions experiences a shift of the laser frequency during a prolonged period when $O_2$ is not present in the sample stream, such an occurrence can negatively impact the performance of the instrument when $O_2$ does occur during a process upset. This can lead to erroneous readings and potential failure of the instrument to properly warn of a safety hazard.

Because the target analyte is always present in the validation cell in instruments consistent with the current subject matter, periodic validations of the laser frequency stability are readily performed so that the instrument can be routinely maintained in an optimal ready state to detect process upsets such as described above. The validation cell will always provide the spectrometer with a detectable absorption peak, regardless of the analyte concentration in the sample gas stream. In this manner, a spectrometer utilizing a tunable laser light source can lock the laser frequency to a suitable absorption peak at any time, not just when the analyte is present in the sample gas.

Figure 8:
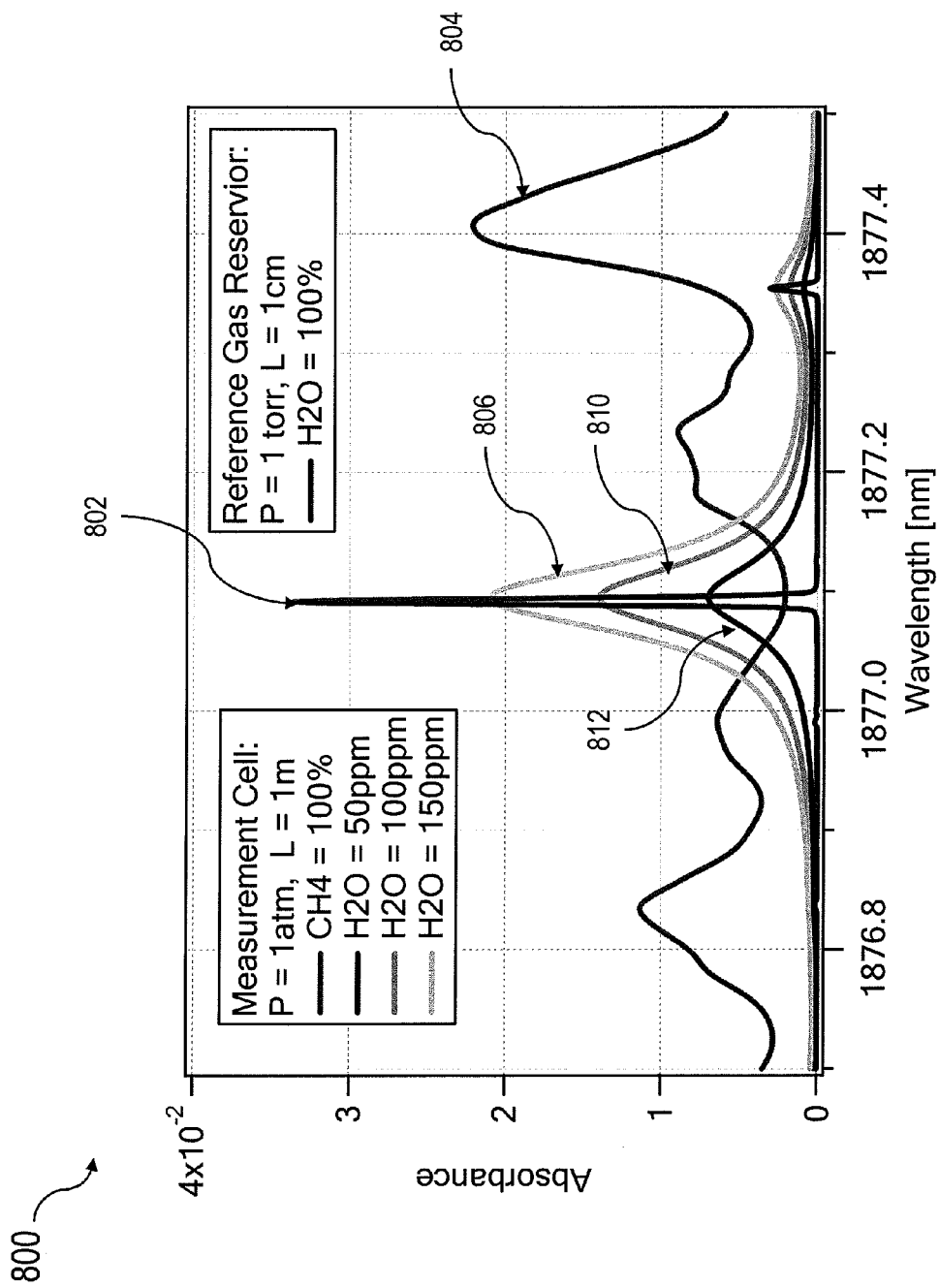
FIG. 8 is a graph comparing absorbance of low pressure water vapor in a validation cell with absorbance of pure methane and different concentrations of water vapor in a sample measurement cell.
Figure 9:
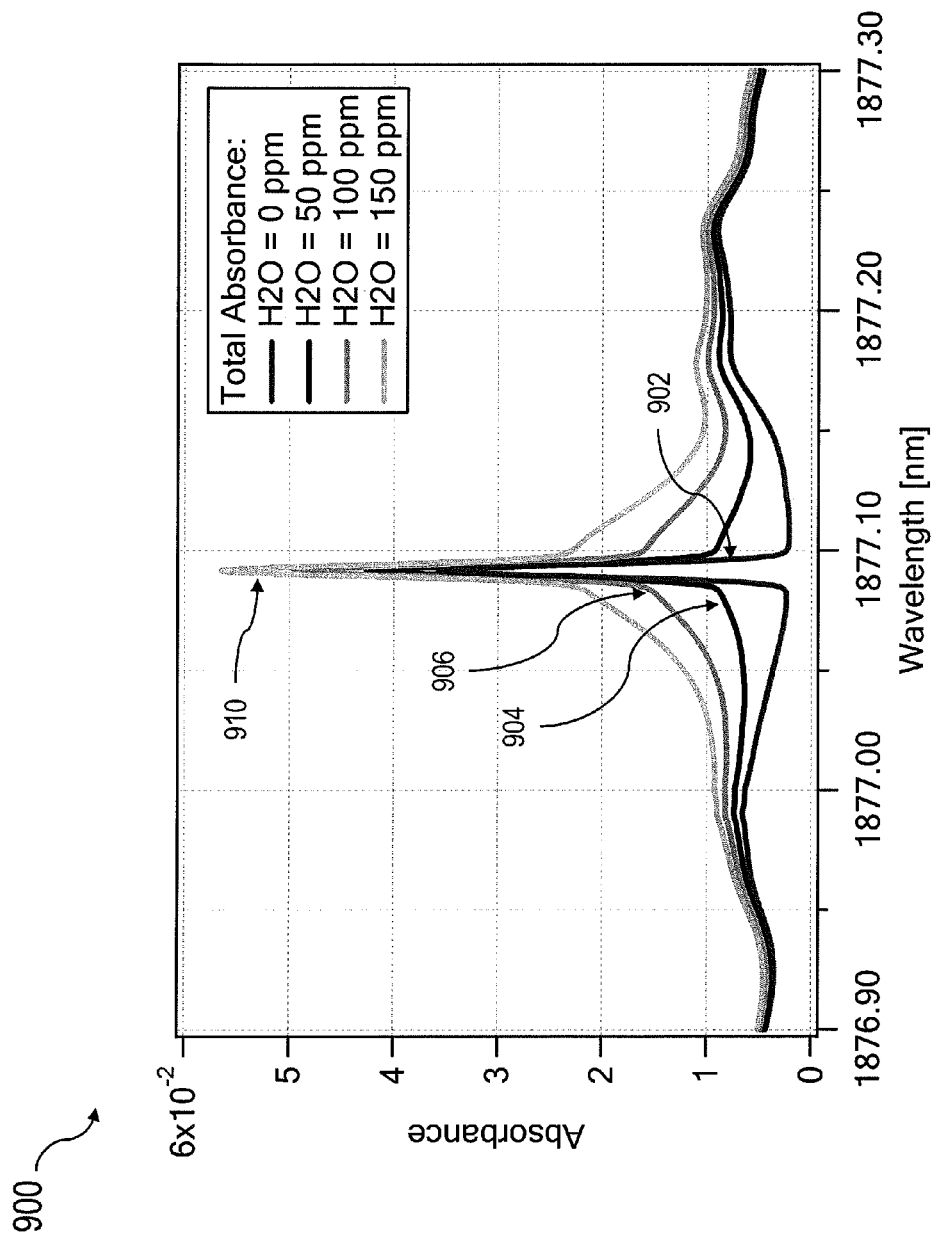
FIG. 9 is a graph showing the total absorbance line shapes for low pressure water vapor in a reference gas cell and different concentrations of water vapor in methane background in a sample measurement cell.

Locking the laser frequency to a suitable molecular absorption peak can provide added operational robustness of the spectrometer against environmental changes and potential aging of the laser light source. FIG. 8 and FIG. 9 show two graphs 700 and 800, respectively, illustrating aspects of peak tracking for measuring trace water vapor in a natural gas or hydrocarbon background. Analysis of such a system has been previously described in co-owned U.S. Pat. Nos. 6,657,198, 7,132,661, 7,339,168, 7,504,631, and 7,679,059 and in pending U.S. Patent Application Publication No. US2004/003877, all of whose disclosures are incorporated herein by reference in their entireties. In an example consistent with at least some implementations of the current subject matter, a validation cell 114 can be filled with neat water vapor at ultra low pressure, such as for example 1 torr. The graph 800 of FIG. 8 shows that the absorption peak of the neat water vapor 802 in the validation cell 114 is much sharper than the absorption spectra of 100% methane gas 804, 50 ppm of water vapor 806, 100 ppm of water vapor 810, or 150 ppm of water vapor 812 at ambient pressure.

As illustrated in the graph 900 of FIG. 9, the sharp absorption peak of the neat water vapor inside the validation cell 114 can be used for reliable peak tracking for concentrations of water vapor in the sample gas stream of at least 0 ppm 902, 50 ppm 904, 100 ppm 906, and 150 ppm 910. The peak 902 at 0 ppm is entirely due to absorbance by the water molecules in the validation cell 114. Subtracting the validation cell spectrum from a sample gas spectrum or otherwise correcting for the absorbance by water vapor in the validation cell 114 can be used to resolve the water vapor concentration in the sample gas, for example that contained in the sample measurement cell 112 during a sample analysis mode.

An alternative to using a zero gas in the free gas space 402 of an open path analytical system 400 or in a contained sample volume of a sample measurement cell 112 of a system that includes a defined sample volume can involve making at least two measurements for a given sample gas at two different temperatures. Because the line shape of the absorbance feature of an analyte can be a function of the pressure of the gas in the validation cell 114 as a consequence of collisional broadening effects, varying the temperature (and as a result the pressure of the sealed volume within the validation cell 114) can lead to the known amount of the analyte in the validation cell 114 creating distinct and distinguishable line shapes that vary as a function of the temperature. As such, by controlling the temperature of the validation cell 114 to two or more known temperatures and comparing the resulting line shapes of the absorbance curves to those collected at a previous time, for example when the instrument is newly calibrated, an indication of the current validation state of the instrument can be readily obtained without the use of any zero gas.

It should be noted that, while various implementations presented herein describe sealed validation cell configurations, the current subject matter also encompasses variations in which the validation cell has a flow-through configuration in which in which a reference gas is continuously or semi-continuously passed through the validation cell. This arrangement may be advantageous for reference gases that can be prepared and stably stored, for example in compressed gas cylinders. Alternatively, a permeation or diffusion source that generates a consistent mass of a trace analyte over time can be used in conjunction with a stream of carrier gas to generate a flowing reference gas for use in such a validation cell.

Using a validation cell 114 as described herein, implementations of the current subject matter can alternatively or in addition provide an automated, algorithmic approach that frequency stabilizes a tunable laser light source of a laser absorption spectrometer to improve the robustness of quantitative trace gas concentration measurements by compensating and/or correcting for short term ambient changes in analytical conditions as well as long term drift and aging effects that may adversely affect performance of the laser absorption spectrometer.

Real time laser frequency stabilization can be achieved in some implementations by comparing actual absorption spectra collected at the time of calibration of an instrument with absorption spectra collected in the field for gas samples without need for providing a bottled reference gas of uncertain concentration stability or using a separate laser frequency stabilization circuit. Aside from increased cost and complexity, a separate laser frequency stabilization circuit can also interfere with the actual measurement. The current subject matter can reduce cost and complexity while also improving operational robustness and measurement fidelity and reproducibility compared to previously available spectroscopy approaches based on frequency stabilization onto a molecular line that is not part of the actual measurement. Using an approach as described herein, information about the performance of a laser spectrometer relative to a previous known or calibrated state can be obtained across the breadth of a scanned wavelength range of a tunable or scannable laser light source. Such an approach can provide substantial improvement relative to techniques that focus only on peak location rather than an entire absorption curve shape over a broader range of wavelengths.

Figure 10:
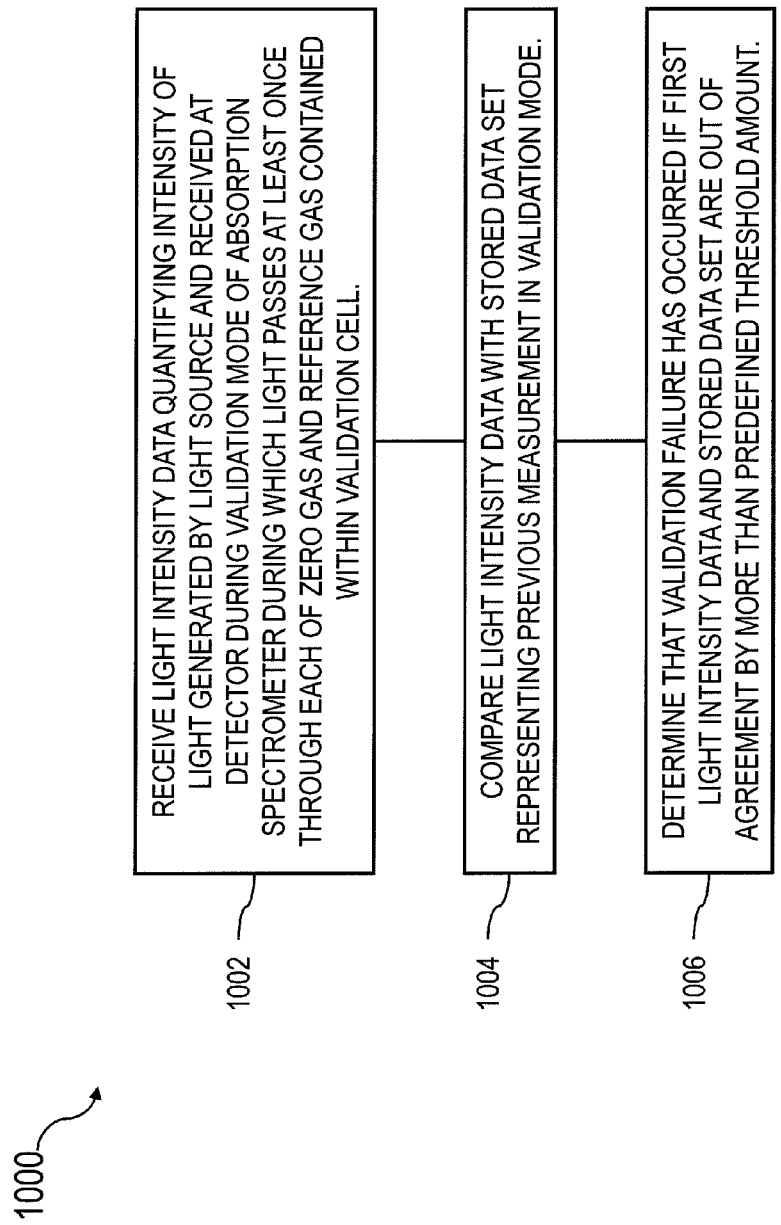
FIG. 10 is a process flow chart illustrating features of a method for determining whether a spectroscopic validation failure has occurred.

FIG. 10 shows a process flow chart 1000 illustrating features of a method that enables determination of a validation failure of an absorption spectrometer. At 1002, light intensity data quantifying intensity of a light beam 104 or other radiation, light, etc. generated by a light source 102 and received at a detector 106 during a validation mode of an absorption spectrometer are received, for example by a controller 122, a programmable processor-based device, or the like. The validation mode can, as discussed above, include causing the light to pass at least once through each of a zero gas and a reference gas, for example a reference gas contained within a validation cell 114 that includes a known amount of a target analyte. The zero gas can be as discussed above and can include at least one of known and negligible first light absorbance characteristics within a range of wavelengths produced by the light source. At 1004, the light intensity data are compared with a stored data set representing at least one previous measurement in the validation mode. A validation failure is determined to have occurred at 1006 if the first light intensity data and the stored data set are out of agreement by more than a predefined threshold amount.

The light source 102 can optionally include a tunable or scannable laser of a laser absorption spectrometer, and the stored data set can include a reference harmonic absorption curve of the laser absorption spectrometer. The reference harmonic absorption curve has a reference curve shape and includes at least one of a first or higher order harmonic signal of a reference signal generated by the detector 106 in response to light passing from the light source 102 through the reference gas in the validation cell 114. The reference harmonic absorption curve can have been previously determined for the laser absorption spectrometer in a known or calibrated state. The light intensity data can include a test harmonic absorption curve having a test curve shape that is collected using the reference gas contained within the validation cell 114 of the absorption spectrometer and zero gas in the sample measurement cell 112 or free gas space 402. The predefined threshold amount can include a predefined allowed deviation between the test curve shape and the reference curve shape.

Figure 11:
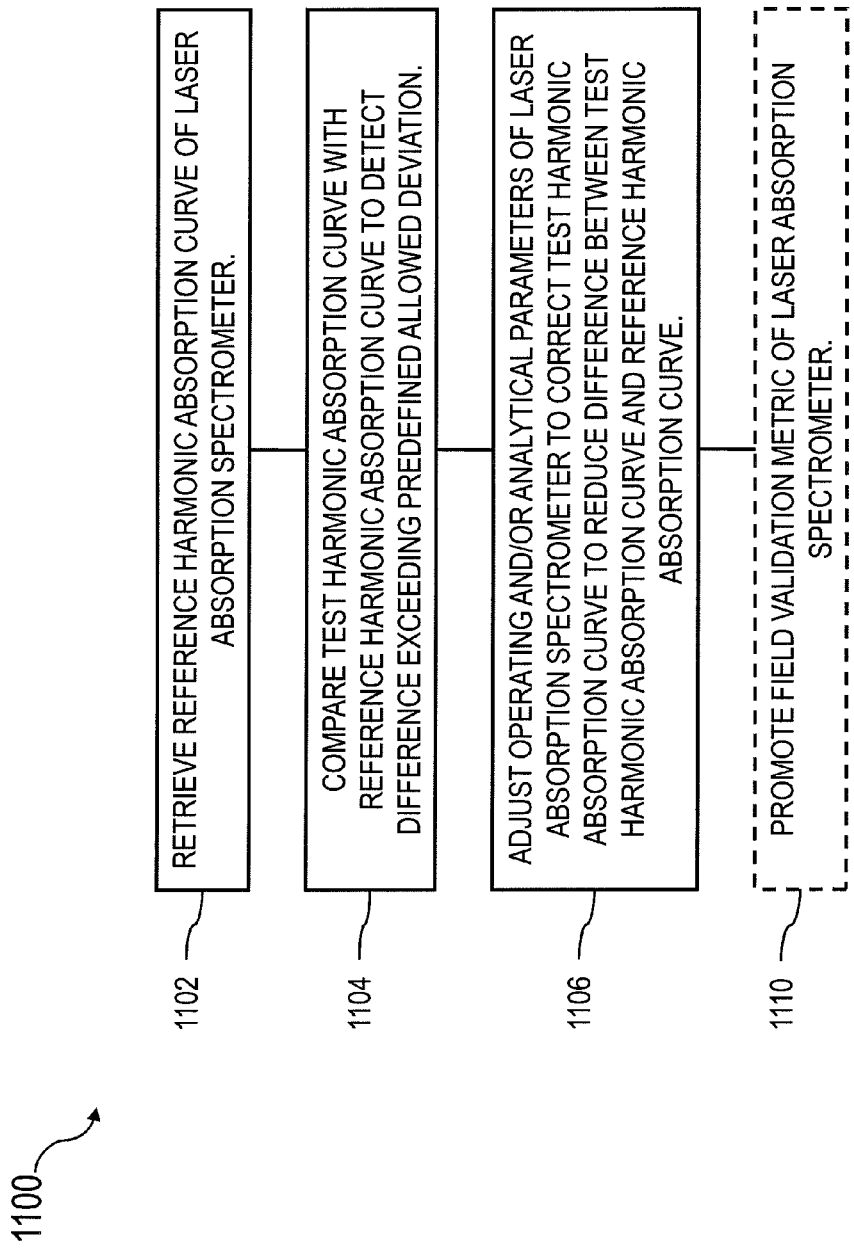
FIG. 11 is a process flow chart illustrating features of a method for determining whether adjusting operating and/or analytical parameters of a laser absorption spectrometer to correct a validation state of the laser absorption spectrometer.

FIG. 11 shows a process flow chart 1100 illustrating additional features consistent with an implementation of the current subject matter. At 1102, one or more reference harmonic absorption curves that can be obtained through analysis of one or more reference gas mixtures by a laser absorption spectrometer is/are retrieved, for example from local or networked data storage. The one or more reference harmonic absorption curves are previously obtained through analysis of one or more reference gas mixtures by a laser absorption spectrometer, for example at factory calibration or at another time when the laser absorption spectrometer is in a well-calibrated state, and stored for later retrieval. At 1104, a test harmonic absorption curve is compared with the at least one of the one or more reference harmonic absorption curves to detect a difference between the respective curve shapes that exceeds a predefined allowed deviation. At 1106, the operating and/or analytical parameters of the laser absorption spectrometer are adjusted to correct the test harmonic absorption curve to reduce the detected difference between the test harmonic absorption curve shape and the reference harmonic absorption curve shape. In other words, after adjusting of the one or more operating and/or analytical parameters of the laser absorption spectrometer, a subsequent test harmonic absorption curve more closely resembles the reference harmonic absorption curve. Optionally, at 1110, a field validation metric of the laser absorption spectrometer can be promoted. The field validation metric can include at least one of the difference between the test curve shape and the reference curve shape, an identification of the one or more operating and analytical parameters that were adjusted, and a value by which the one or more operating and analytical parameters were adjusted.

The adjusting of the one or more operating and/or analytical parameters of the laser absorption spectrometer to reduce the detected difference between the test harmonic absorption curve shape and the reference harmonic absorption curve shape can be performed by a variety of approaches. In one implementation, an iterative approach can be used. In one non-limiting implementation, one of several potential operating and/or analytical parameters of the laser absorption spectrometer can be adjusted and a new test harmonic absorption curve generated by the laser absorption spectrometer. Adjustments to the selected parameter can continue with successive generation of new test harmonic absorption curves until a setting of maximum improvement in the difference between a test harmonic absorption curve and the reference harmonic absorption curve is obtained. Then another parameter can be iteratively adjusted in a similar manner until each parameter has been so adjusted. Any algorithm usable for iteratively converging to a multi-variate solution can be used.

The exact shape of the test harmonic absorption curve, and the concentration calculation of the one or more target analytes for which the laser absorption spectrometer is configured to analyze can depend critically upon the laser frequency behavior. The laser frequency behavior can be affected by one or more operating and environmental parameters that can include, but are not limited to the center frequency, the ramp current, the modulation current, and other parameters of the laser light source as well as one or more parameters of the sample cell, detector, demodulator, and the like. At least the operating temperature and the operating current of the laser light source 102 can affect the center frequency of the laser light source 102. The particular frequency changes caused by changes in drive and/or modulation current, temperature, and the like can be quite specific to each individual laser light source 102.

A curve correlation algorithm according to implementations of the current subject matter can generate an error signal whenever the laser frequency changes, (i.e. if the same reference gas that was used to record the original reference trace is periodically analyzed). The reference harmonic absorption curve can be stored once, when the analyzer receives its original calibration in the factory. Alternatively or in addition, the reference harmonic absorption curve can be updated periodically using a differential spectroscopy approach, for example as described in co-owned and co-pending U.S. patent application Ser. No. 12/763,124 to adjust for stream changes, while maintaining a basic reference from the original calibration.

Upon receiving an error signal, an optimization algorithm can engage to adjust or otherwise reset one or more operating and analytical parameters of the laser absorption spectrometer, which can include but are not limited to laser temperature, operating current, modulation current, ramp current, ramp current curve shape during the scan, and other signal detection and conversion parameters, to automatically reconstruct the exact harmonic absorption curve shape as was originally stored during factory calibration.

Figure 12:
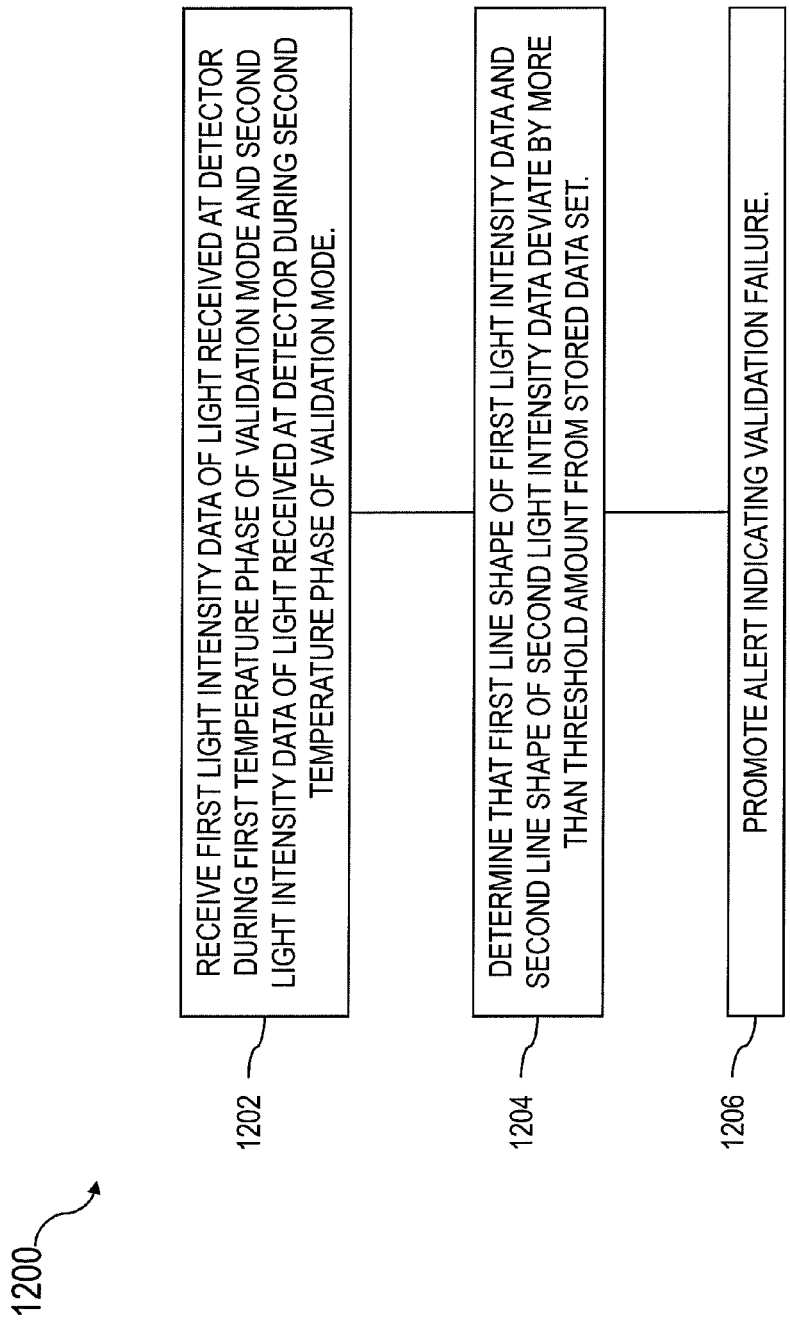
FIG. 12 is a process flow chart illustrating features of a method for determining whether a spectroscopic validation failure has occurred.

In an implementation illustrated in the process flow chart 1200 of FIG. 12, a processor such as a controller 122 can at 1202 receive first light intensity data of a light beam received at a detector during a first phase of a validation mode and second light intensity data of the light beam received at the detector during a second phase of the validation mode. The validation cell 114 can be maintained at a first temperature during the first phase and at a second temperature during the second phase. At 1204, it can be determined that a first line shape of the first light intensity data and a second line shape of the second light intensity data deviate by more than a threshold amount from a stored data set. The stored data set can include previously recorded line shapes for the analyte in the validation cell 114 at the first temperature and the second temperature, respectively. Upon determining that an above-threshold deviation exists, an alert can be promoted at 1206 to indicate that a validation failure has occurred. The promoting of the alert can include one or more of a visible or audible alarm, an alert displayed on a display screen, a transmitted electronic message such as a SMS message or an electronic mail message, a facsimile or audible message over a telephone line or cellular phone link, or any other method for indicating to a local and/or remote user the failure of the validation process.

Another alternative validation method that does not require the use of zero gas in the sample measurement cell 112 or free space 402 is to decompose the total spectra measured during sample analysis into spectra of the reference gas in the validation cell 114, spectra of the target analyte in the sample stream or sample gas contained with the sample measurement cell 112 or in the free space 402 through which the beam 104 from the light source passes on its way to the detector 106, and the spectra of the background. The decomposition can be based on chemometrics or multivariable linear regression to find the best linear combination of the reference spectra for the components of the reference gas in the validation cell 114, target analyte in the sample measurement cell 112 or open space 402, and background components in the sample measurement cell 112 or open space 402. All reference spectra can be recorded during calibration of the analyzer under laboratory or other comparably controlled conditions. In this manner, the validation can be done simultaneously with the sample analysis, removing the blind time for zero gas validation and saving the components switching between sample gas and zero gas.

Figure 13:
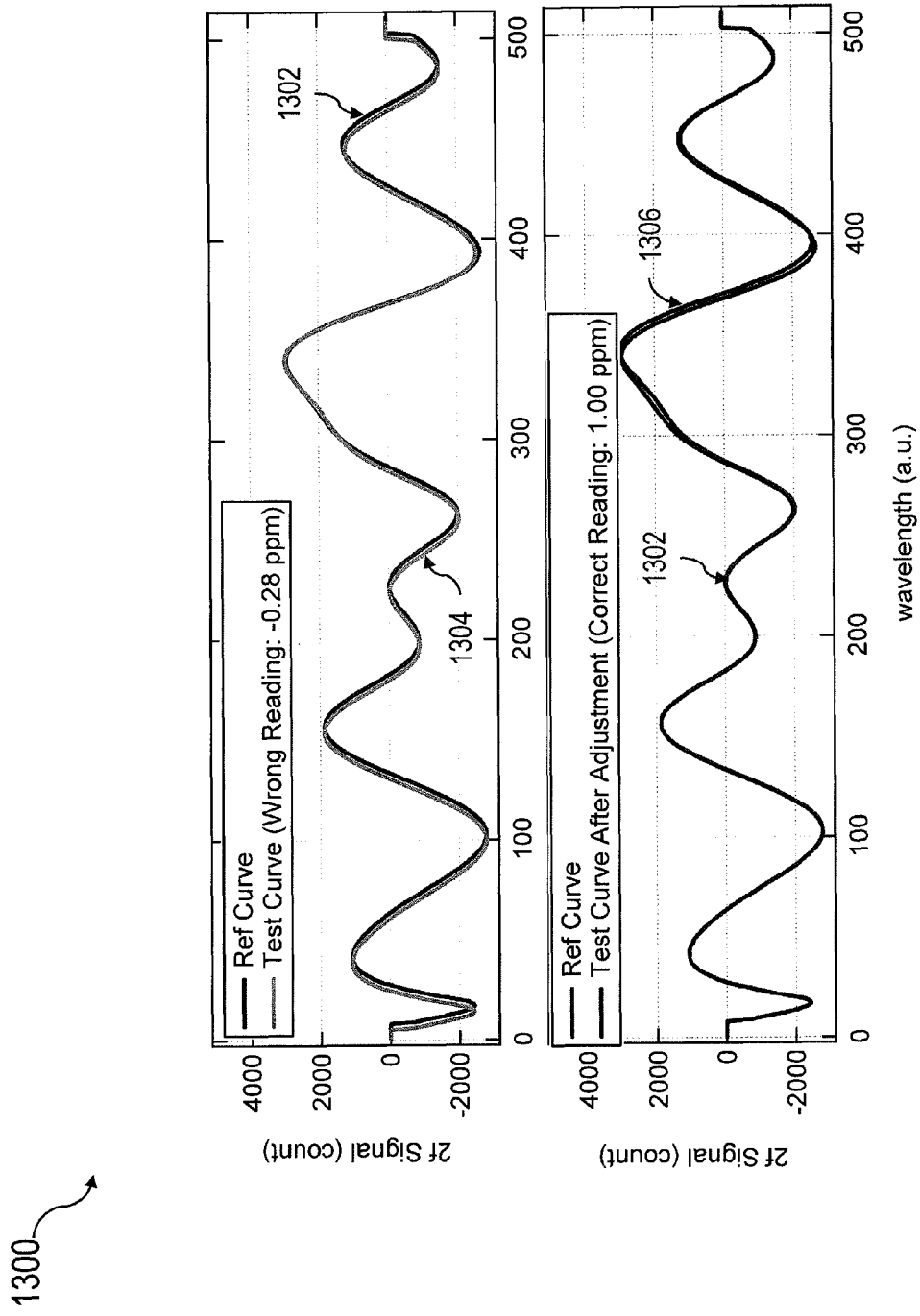
FIG. 13 is a graph illustrating two spectral absorption charts showing an example of adjusting a middle operating current of a laser light source to shift a test curve to align with a stored reference curve.
Figure 14:
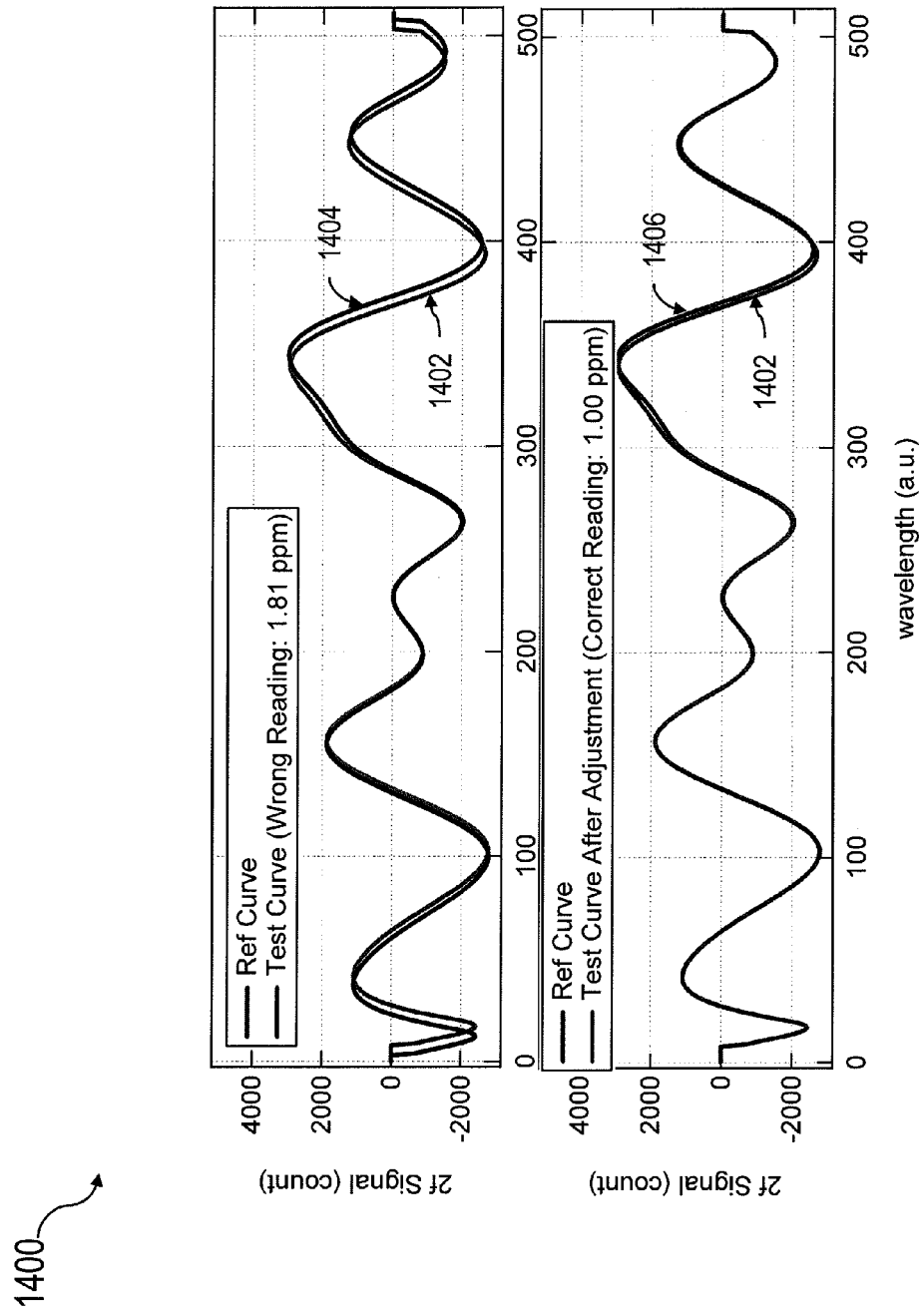
FIG. 14 is a graph illustrating two spectral absorption charts showing an example of adjusting one or more operating parameters of a laser light source and/or signal converting parameters to correct a test curve shape to reduce the difference between the test curve shape and a reference curve shape.

FIG. 13 and FIG. 14 show two examples of dynamic corrections to a calibration state of a spectrometer using sample data. The reference curve 1302 shown in the top and bottom panels of FIG. 13 is obtained with a tunable diode laser spectrometer for a reference gas mixture containing approximately 25% ethane and 75% ethylene. The test curve 1304 shown on the top panel of FIG. 13 is obtained using the same spectrometer after some time had passed for a test gas mixture containing 1 ppm acetylene in a background of approximately 25% ethane and 75% ethylene. Acetylene has a spectral absorption feature in the range of about 300 to 400 on the wavelength axis of the charts in FIG. 13. In an example in which drift and/or other factors affect the spectrometer performance over time, the adjusted test curve 1306 can be shifted (for example to the left as shown in FIG. 2) compared with the reference curve 1302. Absent a correction to the test curve, the measured concentration of acetylene from the spectrometer would be −0.29 ppm instead of the correct value of 1 ppm.

According to an approach consistent with implementations of the current subject matter, the amount of the test curve drift can be identified by comparing the test and reference curves in a portion of the spectrum outside of the area where the acetylene absorption feature occurs (i.e. the region between about 20-260 on the wavelength axis). The laser middle operating current can be adjusted to shift the adjusted test curve 1306 back to align up with the reference curve 1302 as shown in the bottom panel of FIG. 13. After the adjustment, the measured concentration of acetylene from the spectrometer is 1 ppm.

The reference curve in the top and bottom panels of FIG. 14 is also obtained with a tunable diode laser spectrometer for a reference gas mixture containing approximately 25% ethane and 75% ethylene. The test curve 1404 on the top panel of FIG. 14 was obtained for a test gas mixture containing 1 ppm acetylene in a background of approximately 25% ethane and 75% ethylene. As shown in the top panel of FIG. 14, the test curve shape is distorted relative to the shape of the reference curve 1402 due to drift or other factors affecting performance of the laser absorption spectrometer over time. If the test curve 1404 is not corrected, the measured concentration of acetylene in the test gas mixture determined by the spectrometer can be, for example, 1.81 ppm instead of the true concentration of 1 ppm. The bottom panel of FIG. 14 shows the adjusted test curve According to an approach consistent with implementations of the current subject matter, the amount of test curve distortion can be identified and/or corrected for by comparing one or more sections of the test curve 1404 and the reference curve 1402 in one or more portions of the spectrum outside of the area where the acetylene absorption feature occurs (i.e. the regions between about 20-260 and 400-500 on the wavelength axis). The laser operating parameters and signal converting parameters can be adjusted to correct the shape of the adjusted test curve 1406 to more closely resemble the shape of the reference curve 1402. After the adjustment, the measured concentration of acetylene from the spectrometer returns to 1 ppm.

The approaches illustrated in FIG. 13 and FIG. 14 use a reference harmonic spectrum collected for a sample having a background composition consistent with that expected to be present under analytical conditions during which the target analyte (acetylene) is to be quantified. In an alternative or additional implementation, the reference harmonic spectra can be selected to contain one or more background absorption peaks that do not change with background compositions. In an alternative or additional implementation, the reference harmonic spectrum can be constructed from reference absorption spectra of individual background species.

As described and illustrated, implementations of the current subject matter can consider substantially more information regarding the exact shape of a reference harmonic absorption curve than is typically used in peak locking. Previously available laser control loops are generally limited to only stabilizing or tracking the laser frequency and/or peak position (i.e. location of the peak of a spectral feature in the digitized scan range of the measurement).

The approach described herein can be applicable to any laser absorption spectrometer that includes a tunable laser source, including but not limited to direct absorption spectrometers, harmonic absorption spectrometers, differential absorption spectrometers, etc. For a direct absorption spectrometer, the measurement of target analyte concentrations can be performed without using a harmonic conversion or demodulation of the signal obtained from the detector. However, periodic or continuous recalibration of the laser light source, detector, etc. can be performed using a calibration circuit, etc. that makes use of a harmonic signal obtained from the detector signal.

In another implementation, the calibration state of a harmonic absorption spectrometer can be validated using different operating parameters, including but limited to the modulation frequency, ramp frequency, etc., than are used in identifying and/or quantifying a target analyte. Use of larger modulation frequencies can increase the signal to noise ratio of an absorption feature of a target analyte by relatively reducing the impact of absorption by the background composition of a gas mixture. However, as the current subject matter can make use of information obtained from all absorption features that occur across a laser scan range in verifying agreement between a test harmonic absorption curve and a reference harmonic absorption curve, it can be advantageous to collect both the test and reference harmonic absorption curves under conditions that lead to a more complicated spectrum so that additional features are available to be matched between the test and reference harmonic absorption curves.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like. A computer remote from an analyzer can be linked to the analyzer over a wired or wireless network to enable data exchange between the analyzer and the remote computer (e.g. receiving data at the remote computer from the analyzer and transmitting information such as calibration data, operating parameters, software upgrades or updates, and the like) as well as remote control, diagnostics, etc. of the analyzer.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An apparatus comprising:
    a validation cell positioned such that a light path generated by a light source passes through the validation cell at least once in transmission of the light path from the light source to a detector, the validation cell containing a reference gas comprising a known amount of a target analyte;
    a flow switching apparatus to direct a sample gas into the light path during a sample analysis mode and a zero gas into the light path during a validation mode, the zero gas having at least one of known and negligible first light absorbance characteristics within a range of wavelengths produced by the light source; and
    a controller to perform operations comprising:
    receiving light intensity data quantifying intensity of the light received at the detector during the validation mode,
    comparing the light intensity data with a stored data set representing at least one previous measurement in the validation mode; and
    determining that a validation failure has occurred if the first light intensity data and the stored data set are out of agreement by more than a predefined threshold amount.

2. An apparatus as in claim 1, wherein: the light intensity data comprise first light intensity data quantifying the intensity of the light path received at the detector during a first phase of the validation mode in which the validation cell is maintained at a first temperature and second light intensity data of the light path received at the detector during a second phase of the validation mode in which the validation cell is maintained at a second temperature that differs from the first temperature, and the determining that the validation failure has occurred comprises identifying that a first line shape of the first light intensity data and a second line shape of the second light intensity data deviate from a stored data set by a first deviation amount that exceeds a pre-defined threshold amount, the stored data set comprising previously recorded line shapes at the first temperature and the second temperature, respectively.

3. An apparatus as in claim 1, wherein the operations performed by the controller further comprise: promoting an alert that the validation failure has occurred.

4. An apparatus as in claim 1, further comprising: a temperature control apparatus to maintain the validation cell at least at one of the first temperature and the second temperature.

5. An apparatus as in claim 1, further comprising a sample measurement cell to contain an analysis volume, the sample measurement cell being positioned such that the light path passes at least once through each of the analysis volume in the sample measurement cell and the reference gas in the validation cell during transmission of the light path from the light source to the detector.

6. An apparatus as in claim 5, further comprising: an optical cell that comprises the validation cell and the sample measurement cell.

7. An apparatus as in claim 1, wherein the operations performed by the controller further comprise:
    making a first modification to at least one of an operating parameter and an analytical parameter of at least one of the light source, the detector, and the controller in response to the determining that the validation failure has occurred;
    receiving new light intensity data of the light path received at the detector during a repeated validation mode occurring after the first modification of the at least one operating parameter;
    comparing the new light intensity data with the stored data set, and
    determining whether the new light intensity data and the stored data set are out of agreement by more than the predefined threshold amount and if so, whether the new light intensity data and the stored data set are in closer agreement than the light intensity data and the stored data set.

8. An apparatus as in claim 1, wherein
    the light source comprises a tunable or scannable laser of a laser absorption spectrometer, and the stored data set comprise a reference harmonic absorption curve of the laser absorption spectrometer, the reference harmonic absorption curve having a reference curve shape and comprising at least one of a first or higher order harmonic signal of a reference signal generated by the detector in response to the light path passing from the light source through the reference gas in the validation cell, the reference harmonic absorption curve having been determined for the laser absorption spectrometer in a known or calibrated state;
    the light intensity data comprises a test harmonic absorption curve having a test curve shape; and
    the predefined threshold amount comprises a predefined allowed deviation between the test curve shape and the reference curve shape.

9. An apparatus as in claim 8, wherein the operations performed by the controller further comprise:
    adjusting one or more operating and/or analytical parameters of the laser absorption spectrometer to correct the test curve shape to reduce the difference between the test curve shape and the reference curve shape.

10. An apparatus as in claim 9, wherein the one or more operating and/or analytical parameters of the laser absorption spectrometer comprise at least one of laser light source parameters, detector parameters, and signal conversion parameters used in generating the test harmonic absorption curve from a signal produced by the detector.

11. An apparatus as in claim 9, wherein the operations performed by the controller further comprise promoting a field validation metric of the laser absorption spectrometer, the field validation metric comprising at least one of the difference between the test curve shape and the reference curve shape, an identification of the one or more operating and analytical parameters that were adjusted, and a value by which the one or more operating and analytical parameters were adjusted.

12. An apparatus as in claim 9, wherein the laser light source parameters comprise at least one of a temperature, an operating current, a modulation current, a ramp current, a ramp current curve shape, and a phase of the laser light source.

13. An apparatus as in claim 9, wherein the detector parameters comprise at least one of a gain and a phase setting of a detector circuit.

14. An apparatus as in claim 9, wherein the signal conversion parameters comprise at least one of a gain and a phase setting of the demodulating device.

15. An apparatus as in claim 8, wherein the comparing further comprises applying at least one of subtracting, dividing, cross correlation, curve fitting, and multivariable regression for one or more parts or the entire of the test curve and the reference curve, and computing one or more of the difference, the ratio, the mean square error (MSE), the coefficient of determination ($R^2$), the cross correlation function/integral and the regression coefficients in the light intensity (i.e., the y-axis) and/or the wavelength (i.e. the x-axis) domain to quantify the difference between the test curve shape and the reference curve shape.

16. An apparatus as in claim 8, wherein the reference harmonic absorption curve comprises at least one of a calibration reference curve stored during calibration of the laser absorption spectrometer and a constructed curve comprising one or more mathematically combined stored calibration reference curves selected according to at least one of a composition of a background gas that the sample gas comprises and an expected concentration of a target analyte to be measured in the sample gas containing the background gas.

17. An apparatus as in claim 8, wherein the comparing further comprises applying a curve fitting algorithm to quantify the difference between the test curve shape and the reference curve shape.

18. An apparatus as in claim 1, wherein the light path into which the sample gas is directed during the sample analysis mode and into which the zero gas is directed during the validation mode passes through the validation cell at least once.

19. An apparatus as in claim 1, wherein the known amount of the analyte in the reference gas is a non-zero amount.

20. An apparatus as in claim 1, wherein the sample gas directed into the light path during the sample analysis mode and the zero gas directed into the light path during the validation mode are not contained within the validation cell.

21. A method comprising:
comparing light intensity data with a stored data set representing at least one previous measurement in a validation mode of an absorption spectrometer; the light intensity data quantifying intensity of a light path generated by a light source and received at a detector during the validation mode of the absorption spectrometer, the validation mode comprising causing the light path to pass at least once through each of a zero gas and a reference gas, the reference gas being contained within a validation cell and comprising a known amount of a target analyte, the zero gas having at least one of known and negligible first light absorbance characteristics within a range of wavelengths produced by the light source; and
determining that a validation failure has occurred if the first light intensity data and the stored data set are out of agreement by more than a predefined threshold amount;
wherein the comparing and the determining are performed by at least one system comprising computer hardware.

22. A method as in claim 21, wherein:
the light source comprises a tunable or scannable laser of a laser absorption spectrometer, and the stored data set comprise a reference harmonic absorption curve of the laser absorption spectrometer, the reference harmonic absorption curve having a reference curve shape and comprising at least one of a first or higher order harmonic signal of a reference signal generated by the detector in response to the light path passing from the light source through the reference gas in the validation cell, the reference harmonic absorption curve having been determined for the laser absorption spectrometer in a known or calibrated state;
the light intensity data comprises a test harmonic absorption curve having a test curve shape; and
the predefined threshold amount comprises a predefined allowed deviation between the test curve shape and the reference curve shape.

23. A method as in claim 22, further comprising: adjusting one or more operating and/or analytical parameters of the laser absorption spectrometer to correct the test curve shape to reduce the difference between the test curve shape and the reference curve shape.

24. A method as in claim 23, wherein the one or more operating and/or analytical parameters of the laser absorption spectrometer comprise at least one of laser light source parameters, detector parameters, and signal conversion parameters used in generating the test harmonic absorption curve from a signal produced by the detector.

25. A method as in claim 24, wherein:
the laser light source parameters comprise at least one of a temperature, an operating current, a modulation current, a ramp current, a ramp current curve shape during scanning and a phase of the laser light source; the detector parameters comprise at least one of a gain and a phase setting of a detector circuit; and the signal conversion parameters comprise at least one of a gain and a phase setting of the demodulating device.

26. An article comprising a non-transitory computer readable medium encoding instructions that, when executed by at least one processor, cause the at least one processor to perform operations comprising:
comparing light intensity data with a stored data set representing at least one previous measurement in a validation mode of an absorption spectrometer; the light intensity data quantifying intensity of a light path generated by a light source and received at a detector during the validation mode of the absorption spectrometer, the validation mode comprising causing the light path to pass at least once through each of a zero gas and a reference gas, the reference gas being contained within a validation cell and comprising a known amount of a target analyte, the zero gas having at least one of known and negligible first light absorbance characteristics within a range of wavelengths produced by the light source; and
determining that a validation failure has occurred if the first light intensity data and the stored data set are out of agreement by more than a predefined threshold amount.

27. An article as in claim 26, wherein:
the light source comprises a tunable or scannable laser of a laser absorption spectrometer, and the stored data set comprise a reference harmonic absorption curve of the laser absorption spectrometer, the reference harmonic absorption curve having a reference curve shape and comprising at least one of a first or higher order harmonic signal of a reference signal generated by the detector in response to the light path passing from the light source through the reference gas in the validation cell, the reference harmonic absorption curve having been determined for the laser absorption spectrometer in a known or calibrated state;
the light intensity data comprises a test harmonic absorption curve having a test curve shape; and
the predefined threshold amount comprises a predefined allowed deviation between the test curve shape and the reference curve shape.

* * * * *